(12) United States Patent
Yokogawa et al.

(10) Patent No.: US 8,197,774 B2
(45) Date of Patent: Jun. 12, 2012

(54) MICROCHIP

(75) Inventors: Akinori Yokogawa, Kyoto (JP); Shun Momose, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 545 days.

(21) Appl. No.: 12/343,973

(22) Filed: Dec. 24, 2008

(65) Prior Publication Data
US 2009/0232708 A1 Sep. 17, 2009

(30) Foreign Application Priority Data

Dec. 27, 2007 (JP) ................. 2007-337274
Dec. 28, 2007 (JP) ................. 2007-339571

(51) Int. Cl.
*G01N 1/38* (2006.01)
*B04B 5/00* (2006.01)

(52) U.S. Cl. ........ 422/506; 422/501; 422/502; 422/503; 422/504; 422/507

(58) Field of Classification Search .......... 422/501–504, 422/506, 507
See application file for complete search history.

(56) References Cited

U.S. PATENT DOCUMENTS

| | | | |
|---|---|---|---|
| 4,883,763 A | 11/1989 | Holen et al. | |
| 2007/0243111 A1* | 10/2007 | Momose | 422/100 |
| 2008/0156079 A1 | 7/2008 | Momose et al. | |
| 2008/0296734 A1 | 12/2008 | Momose | |
| 2009/0084738 A1 | 4/2009 | Momose | |
| 2009/0098658 A1 | 4/2009 | Momose et al. | |
| 2009/0104077 A1 | 4/2009 | Momose | |
| 2009/0111675 A1 | 4/2009 | Yokogawa et al. | |
| 2009/0135407 A1 | 5/2009 | Kageyama et al. | |
| 2009/0142232 A1 | 6/2009 | Okada et al. | |
| 2009/0155125 A1 | 6/2009 | Michiue et al. | |

FOREIGN PATENT DOCUMENTS

| | | |
|---|---|---|
| JP | 2006-300741 | 11/2006 |
| JP | 2007-298474 | 11/2007 |

OTHER PUBLICATIONS

U.S. Appl. No. 12/467,404, filed May 18, 2009.
U.S. Appl. No. 12/424,913, filed Apr. 16, 2009.

* cited by examiner

*Primary Examiner* — In Suk Bullock
*Assistant Examiner* — Paul Hyun
(74) *Attorney, Agent, or Firm* — Fish & Richardson P.C.

(57) ABSTRACT

A microchip is provided, in which dead space provided only for holding excess fluid is made smaller. The microchip is formed by joining at least a first substrate with a trench formed on the substrate surface and a second substrate, and it has a fluid circuit formed by the trench and a surface of the second substrate facing the first substrate. The first substrate and/or the second substrate has a projection for moving fluid and/or air in a direction opposite to the direction of gravity during an operation of the microchip, and the projection is provided near an end portion of a through hole and/or an air vent.

9 Claims, 22 Drawing Sheets

MICROCHIP

BACKGROUND OF THE INVENTION

1. Field of the Invention

The present invention relates to a microchip useful as a μ-TAS (Micro Total Analysis System) used for environmental analysis, chemical synthesis and biochemical inspection of DNA, protein, cells, immunity, blood and the like and, more specifically, to a microchip for inspection and analysis utilizing optical examination.

2. Description of the Background Art

Recently, in the field of medical, health, food and drug discovery, importance of sensing, detecting and determining quantity of chemical substance and biological matter such as DNA (Deoxyribo Nucleic Acid), enzyme, antigen, antibody, protein, viruses and cells has been increasing, and various biochips and micro chemical chips (hereinafter generally referred to as microchips) allowing easy examination of these have been proposed. The microchip enables a series of experiments/analysis operations, which has been conducted in a laboratory, within a chip having the size of a few centimeters to ten centimeters square and the thickness of a few millimeters to a few centimeters. Therefore, it is advantageous in many aspects. For example, it requires small amount of specimen and reagent, its cost is low, reaction speed is fast and hence inspection with high throughput is possible, and the result of inspection can be provided at the site where the specimen is taken.

A microchip has a fluid circuit therein, and the fluid circuit mainly consists of various sections including: a liquid reagent holding section holding liquid reagent for processing a specimen (such as blood) or for causing a reaction with the specimen or to be mixed with the specimen; a measuring section for measuring the specimen or liquid reagent; a mixing section for mixing the specimen with the liquid reagent; a detecting section for analyzing/inspecting the mixed liquid; and fine fluid circuit (having the width of, for example, a few hundred μm), appropriately connecting these sections to each other. Typically, a microchip is used mounted on an apparatus that can impart centrifugal force to the chip (centrifuge). By applying centrifugal force in an appropriate direction to the microchip, specimen and liquid reagent are measured and mixed, and the mixed liquid can be introduced to the detecting section. The mixed liquid introduced to the detecting section can be inspected and analyzed (for example, a specific component in the mixed liquid can be detected) by optical examination, for example, by irradiating the detecting section containing the mixed liquid with detecting light and examining transmittance thereof (see Japanese Patent Laying-Open Nos. 2006-300741 and 2007-298474).

Here, microchips can roughly be divided, from their shapes, into two types. One is the type (in the following, also referred to as a first type) in which the fluid circuit is formed by joining a substrate having a trench on one surface with another substrate. The other is the type (in the following, also referred to as a second type) in which fluid circuit is formed by joining a substrate having trenches on opposite surfaces with separate substrates on the opposite surfaces.

Microchips of both former and latter types have an air vent to allow smooth movement of liquid through the fine fluid circuit. The air vent connects the fluid circuit to the outside and, in designing a microchip, it must be provided at such a position where leakage of liquid from the air vent can be prevented.

FIG. 26 is a schematic perspective view showing an example of the measuring section and an excess storage of a conventional microchip. FIG. 27 is a schematic perspective view showing another example of the measuring section and an excess storage of a conventional microchip. Microchips shown in FIGS. 26 and 27 are of the first type.

In the following, description will be given with reference to FIGS. 26 and 27. First, the microchip shown in FIG. 26 will be described. The microchip includes a measuring section 80 and an excess storage 74, with an air vent provided at a position 72. In the microchip, a specimen, liquid reagent or mixture (hereinafter, these may simply be referred to as "fluid") is introduced from a flow path 71 by the application of centrifugal force, and a prescribed amount thereof is measured at measuring section 80. The fluid overflowed from measuring section 80 flows as excess fluid, to excess storage 74. Centrifugal force is first applied in the left direction of FIG. 26, and thereafter, centrifugal force is applied in the upward direction of FIG. 26, whereby the fluid in measuring section 80 moves upward in FIG. 26, and the excess fluid is reserved in excess storage 74. In order to realize such a series of fluid operations, an air vent is provided near the position 72. The vent is positioned not directly above the fluid in operation, but at a position connected to the fluid circuit. In other words, it is necessary to enclose the excess fluid in a maze-like excess storage 74 so that the excess fluid would not flow out from the air vent even when centrifugal force is applied in four directions, for example, and to provide the air vent separately at a portion where contact with the fluid is impossible. The structure shown in FIG. 26 may hinder reduction in size of the microchip.

Next, the microchip shown in FIG. 27 will be described. The microchip includes a measuring section 90 and an excess storage 84, with an air vent provided at position 82. In the microchip, the fluid is introduced from a flow path 81 by the application of centrifugal force, and a prescribed amount thereof is measured at measuring section 90. The fluid overflowed from measuring section 90 flows as excess fluid, to excess storage 84. Next, centrifugal force is applied in the left direction of FIG. 27, so that the fluid in measuring section 90 moves to a next, functioning section, while the excess fluid moves to the left side of excess storage 84 of FIG. 27. Next, centrifugal force is applied in the upward direction of FIG. 27, whereby excess fluid moves upward in FIG. 27 and the excess fluid is reserved in excess storage 84. In order to realize such a series of fluid operations, an air vent is provided near the position 82. The vent is positioned not directly above the fluid in operation, but at a position connected to the fluid circuit. In other words, however, the air vent must be provided near the center of excess storage 84 so that the fluid would not pass directly above the air vent even if centrifugal force is applied in four directions. Therefore, around the air vent, so-called dead spaces result, for holding the excess fluid when centrifugal force is applied in respective four directions. Therefore, the structure shown in FIG. 27 possibly hinders reduction in size of the microchip.

A structure that can make smaller the dead space for excess fluid or the like has been developed also for the microchips of the second type.

In a microchip, an excess storage is provided for containing excess fluid such as specimen or liquid reagent that is determined to be excessive in measuring of specimen and liquid reagent and hence unnecessary for examination. In order not to affect the examination above after once contained in the excess storage, the excess fluid must be kept in the excess storage. Therefore, a microchip having an excess storage occupying a certain area has been disclosed (for example, see U.S. Pat. No. 4,883,763).

FIG. 28 is a schematic perspective view showing an example of a conventional excess storage of a microchip. FIG. 29 is a schematic plan view showing an example of a conventional excess storage of a microchip. The dimensional relation of length, size and width in the figures are appropriately changed for simplicity and clarification and does not represent actual size.

In the following, the structure and operation of conventional excess storage will be described with reference to FIGS. 28 and 29. The microchip shown in FIG. 28 is formed by joining a first substrate 251 and a second substrate 252, and a trench is formed on a surface of first substrate 251. The trench and that surface of second substrate 252 which faces the first substrate 251 form the fluid circuit. The fluid circuit has a flow path 253 and an excess storage 255 coupled to flow path 253. Specifically, by the trench formed on the surface of first substrate 251 and the second substrate 252, flow path 253 and excess storage 255 are formed. The microchip may or may not have an air vent 256 formed therein.

In the microchip shown in FIGS. 28 and 29, excess fluid as the fluid in flow path 253 is moved by applying centrifugal force in the direction indicated by an arrow 263, next in the direction of arrow 262, next in the direction of arrow 261, and thereafter in the direction of arrow 264, thereby the excess fluid can be moved to and contained in excess storage 255. Thereafter, unless the centrifugal force is applied in the direction of arrows 261, 262, 263 and 264 in this order during the operation of the microchip, the excess fluid will not flow back, and the excess fluid is kept contained in excess storage 255.

In other words, however, if a conventional excess storage of such a structure is used, the excess fluid contained in excess storage 255 would flow back unless the order of applying centrifugal force is regulated during the operation of microchip. Further, excess storage 255 having an eddy shape when viewed two-dimensionally such as shown in FIG. 29 occupies a considerable area of the microchip, limiting reduction in size of the microchip.

SUMMARY OF THE MENTION

The present invention was made to solve the above-described problems, and its object is to provide a microchip in which dead space provided only for holding excess fluid is made smaller.

Another object is to provide a microchip in which excess fluid never flows back no matter in what order the centrifugal force is applied to the microchip after the excess fluid is once contained in the excess storage, and further to provide a microchip in which the area occupied by the excess storage is set smaller than in a conventional example.

The present invention is directed to a microchip formed by joining at least a first substrate with a trench formed at the substrate surface and a second substrate, having a fluid circuit formed by the trench and a surface of the second substrate facing the first substrate, wherein a projection for moving fluid and/or air in a direction opposite to direction of gravity during an operation of the microchip is provided on the first substrate and/or the second substrate; and the projection is provided near an end portion of a through hole and/or an air vent.

Further, the present invention is directed to a microchip formed by joining at least a second substrate, a first substrate and a third substrate in this order, wherein the first substrate has trenches formed on opposite surfaces; the microchip having a first fluid circuit formed by the trench and a surface of the second substrate facing the first substrate, and a second fluid circuit formed by the trench and a surface of the third substrate facing the first substrate; wherein the first substrate has a through hole connecting the first fluid circuit and the second fluid circuit; the microchip including a projection formed in the vicinity of the through hole, on the surface of the first substrate, in the second fluid circuit.

Preferably, the microchip further includes a first wall surface connecting the surface of the first substrate forming the first fluid circuit and an inner wall forming the through hole, and shutting off the first fluid circuit, and the first wall surface and the inner wall forming the through hole are inclined in a direction to the third substrate.

Preferably, the microchip includes at least two such projections.

In the microchip, preferably, a surface forming the projection is inclined in a direction to the third substrate.

Further, the present invention is directed to a microchip formed by joining at least a first substrate with a trench formed at the substrate surface and a second substrate, having a fluid circuit formed by the trench and a surface of the second substrate facing the first substrate, wherein the second substrate has an air vent connecting the fluid circuit to the outside of the microchip; the microchip having a projection near the air vent, on a surface of the second substrate, in the fluid circuit.

Further, in the microchip, preferably, a surface forming the projection is inclined in a direction to the first substrate.

Further, the present invention is directed to a microchip formed by joining at least a first substrate with a trench formed at the substrate surface and a second substrate, having a fluid circuit formed by the trench and a surface of the second substrate facing the first substrate, wherein the first substrate has an air vent connecting the fluid circuit to the outside of the microchip; the microchip having a projection near the air vent, on a surface of the first substrate, in the fluid circuit.

Further, in the microchip, preferably, a surface forming the projection is inclined in a direction to the second substrate.

The present invention is directed to a microchip formed by joining a second substrate, a first substrate and a third substrate in this order, wherein the first substrate has trenches formed on opposite surfaces; the microchip having a first fluid circuit formed by the trench and a surface of the second substrate facing the first substrate, and a second fluid circuit formed by the trench and a surface of the third substrate facing the first substrate; wherein the first substrate has a through hole connecting the first fluid circuit and the second fluid circuit; the microchip having a projection extended over a surface of the second fluid circuit on the side of the first substrate, with an inner surface forming a through hole; wherein fluid moves from the second fluid circuit to the first fluid circuit and the fluid that has moved to the second fluid circuit does not move to the first fluid circuit, during an operation of the microchip; and cross-section of the through hole in a direction parallel to the microchip is smaller than cross-section of the first fluid circuit in a direction parallel to the microchip.

Further, the present invention is directed to a microchip formed by joining at least a third substrate, a first substrate having trenches formed on opposite surfaces and a second substrate in this order, and having a fluid circuit formed by the trench and a surface of the second substrate facing the first substrate, and a fluid circuit formed by the trench and a surface of the third substrate facing the first substrate; wherein the fluid circuit at least has an excess storage provided inside the first substrate, a first flow path for introducing fluid to the excess storage, and a coupling flow path coupling the excess storage and the first flow path; opposite ends of the coupling flow path are coupled to an end portion of the first flow path and to a surface forming the excess storage, respectively; and the end portion of the first flow path and the surface forming the excess storage are positioned at different positions in thickness direction of the microchip.

Preferably, the microchip in accordance with the present invention further includes a third substrate, wherein the first substrate has trenches formed on opposite surfaces, and by joining the third substrate, the fluid circuit is formed by the trench and the surface of the third substrate facing the first substrate.

Further, in the microchip of the present invention, preferably, the coupling flow path is formed substantially at a center of the surface forming the excess storage.

Further, in the microchip of the present invention, preferably, the coupling flow path is formed in a direction approximately parallel to the thickness direction of the first substrate.

A microchip including an air vent and/or through hole with the dead space made smaller can be provided, while leakage of fluid to the outside of the microchip can be prevented.

Further, in the microchip in accordance with the present invention, no matter in what order the centrifugal force is applied after the excess fluid is contained in the excess storage, backflow of excess fluid does not occur, and the area occupied by the excess storage can be set smaller.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
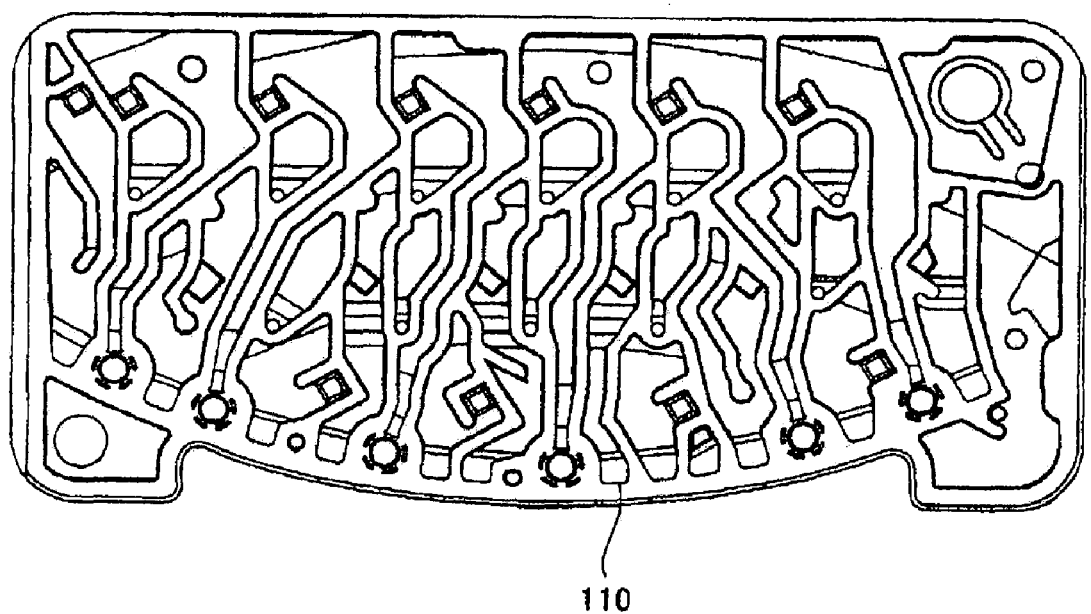
FIG. 1 is a schematic plan view showing an example of a first substrate of a microchip in accordance with the present invention.

The present invention relates to a microchip having a fluid circuit therein. The microchip in accordance with the present invention is formed by at least a first substrate having a trench formed on the substrate surface and a second substrate joined to the surface having the trench of the first substrate, and by the trench formed on the surface of the first substrate and the joined surface of the second substrate, the fluid circuit is formed. Though not specifically limited, the microchip has length and width of about few cm and the thickness of a few mm to about 1 cm. The microchip in accordance with the present invention may also have a third substrate, the first substrate may have trenches on opposite surfaces, the third substrate is joined and thereby a fluid circuit may be formed by the trench and the surface of the third substrate facing the first substrate. In the microchip of the present invention, the shape of detecting section and the like known in a conventional microchip is not specifically limited.

The fluid circuit may have other section or sections in addition to the detecting section. Though not limited, the other section may include a liquid reagent holding section for holding a liquid reagent, measuring sections for measuring the liquid reagent and the specimen introduced to the fluid circuit (or a specific component in the specimen, hereinafter also simply referred to as the specimen), respectively, and a mixing section for mixing the measured liquid reagent and the specimen, as known in a conventional microchip. Additional sections may also be provided as needed. The object of inspection and analysis (object sample) using the microchip having such sections in the fluid circuit is, typically, a mixture of the specimen and liquid reagent. Here, the liquid reagent refers to a reagent that processes the specimen or that is mixed or reacted with the specimen as the object of inspection and analysis using the microchip. Generally, the reagent is introduced and held in the liquid reagent holding section of the fluid circuit in advance, before using the microchip.

Various sections in the fluid circuit are arranged at appropriate positions and connected to each other through fine fluid circuit (hereinafter also simply referred to as the fluid circuit) such that measuring of the specimen and liquid reagent, mixing of the specimen and liquid reagent, introduction of the resulting mixture (object sample) to the detecting section, and inspection and analysis of the mixture (object sample) are performed successively, by applying centrifugal force from the outside. Application of centrifugal force to the microchip is typically executed by mounting the microchip on an apparatus (centrifuge) that can apply centrifugal force thereto.

The fluid circuit includes an excess storage provided inside the first substrate, for containing specimen and liquid reagent determined, in measuring the specimen and the liquid reagent, to be excessive and unnecessary for examination. The fluid circuit further includes a first flow path for introducing the fluid to the excess storage, and a coupling path coupling the excess storage and the first flow path. The excess fluid contained in the excess storage never flows back to the first flow path during the operation of microchip.

In the following, embodiments of the present invention will be described with reference to the figures. In the figures, the same or corresponding portions are denoted by the same reference characters, and description thereof will not be repeated. Further, the dimensional relation of length, size and width in the figures are appropriately changed for simplicity and clarification of the figures, and does not represent actual size.

The microchip in accordance with the present invention at least includes a first substrate and a second substrate to be joined to the first substrate. It may further include a third substrate, to be joined to the surface of the first substrate opposite to the surface to be joined to the second substrate. The first substrate has a trench formed on the substrate surface. In the present invention, the first substrate may have trenches on opposite surfaces, or it may have a trench or trenches only on one surface. The microchip has at least a fluid circuit formed by the trench and the surface of the second substrate facing the first substrate. Specifically, the microchip in accordance with the present invention may be either of the first type or the second type mentioned above.

In the present invention, the first substrate and/or the second substrate includes a through hole and/or an air vent, for moving the fluid and/or air in a direction opposite to the direction of gravity during microchip operation, and near the end of through hole and/or air vent, a projection is provided.

Figure 2:
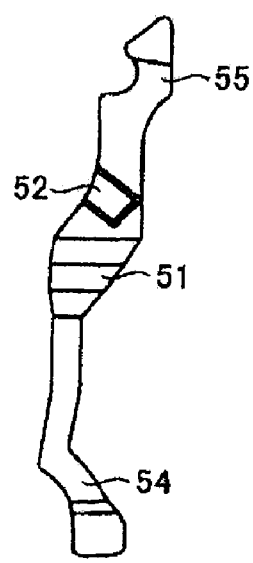
FIG. 2 is an enlarged view of a portion of the first substrate shown in FIG. 1.

FIG. 1 is a schematic plan view showing an example of the first substrate of the microchip in accordance with the present invention. FIG. 2 is an enlarged view of a portion 110 of the first substrate shown in FIG. 1.

In the following, description will be given with reference to FIGS. 1 and 2. FIGS. 1 and 2 specifically show an example in which the first substrate with trenches on opposite surfaces includes a through hole 52 passing through the thickness direction of the microchip, a projection 51, a first excess storage 54, and a second excess storage 55. Specifically, the first substrate has trenches formed on both surfaces thereof, and through hole 52 formed to pass through in the thickness direction. By joining the second and third substrates therewith, two layers of fluid circuits are formed inside the microchip. One of the two layers of fluid circuits, that is, the second flow path as will be described later forms the first excess storage 54 and the second excess storage 55. Here, two layers mean that fluid circuits are formed at two positions different in the thickness direction of the microchip. The "through hole" shown in FIGS. 1 and 2 will be described in detail with reference to the second embodiment. In the following, structure of the fluid circuits formed at the surface of first substrate and the shape of through hole and air vent will be described in detail.

First Embodiment

Figure 3:
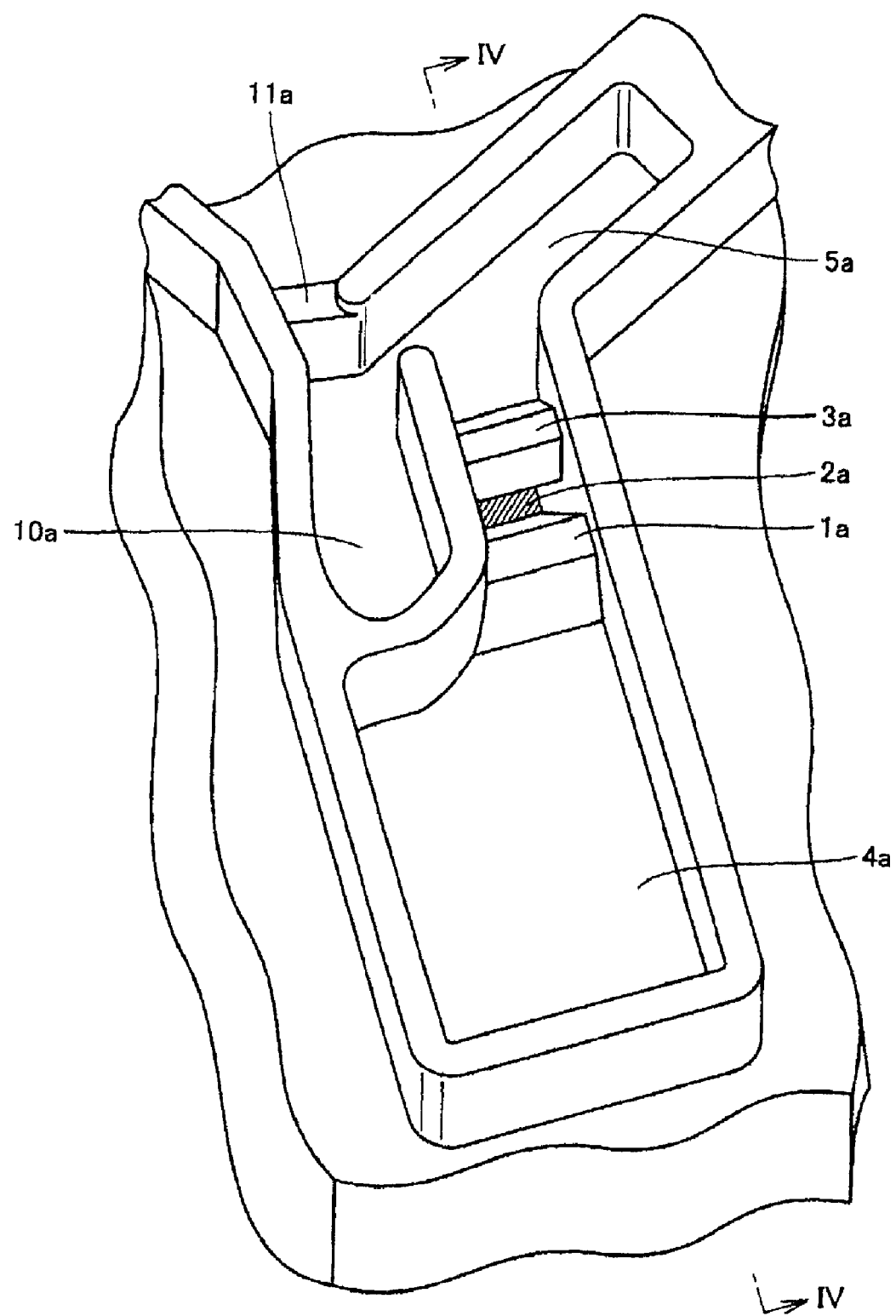
FIG. 3 is a perspective view of a portion of a microchip in accordance with a first embodiment.
Figure 4:
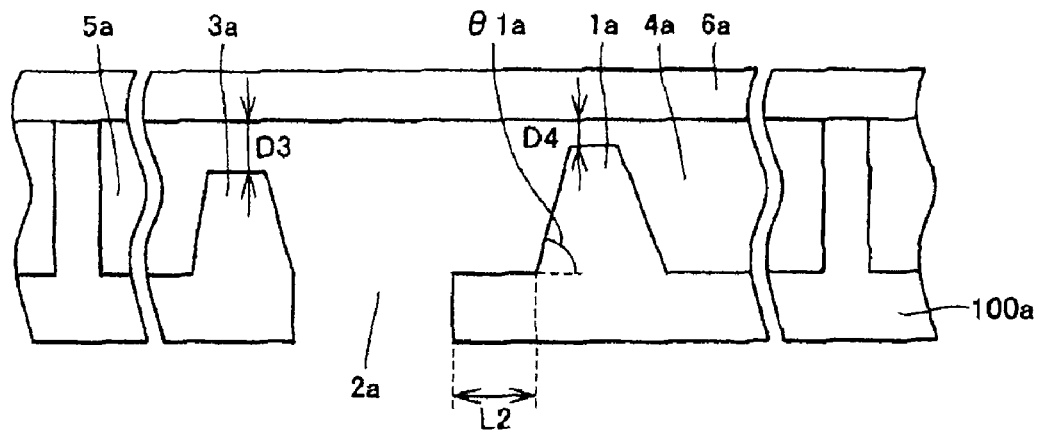
FIG. 4 is a cross-section taken along the line IV-IV of FIG. 3.

FIG. 3 is a perspective view of a portion of the microchip in accordance with the present embodiment. FIG. 4 is a cross-section taken along the line IV-IV of FIG. 3. FIGS. 5A to 7B are schematic cross-sections showing the operation of fluid in the microchip in accordance with the present embodiment.

In the following, description will be given with reference to FIGS. 3 to 7B. In the present embodiment, "upper in the thickness direction" refers to the direction to the second substrate 6a in the thickness direction, and "lower in the thickness direction" refers to the direction to the first substrate 100a in the thickness direction.

First, a simple operation of the microchip will be described with reference to FIGS. 3 and 4. In the microchip, the fluid is introduced through flow path 11a by the application of centrifugal force, and a prescribed amount is measured by measuring section 10a. Further, the fluid unnecessary for the detection by the microchip, that is, the so-called excess fluid, is introduced to the second fluid circuit 4a.

Next, the structure of microchip will be described. The microchip in accordance with the present invention is formed by joining, in order, the second substrate 6a to the first substrate 100a. In FIG. 3, the second substrate 6a is omitted for convenience. The first substrate 100a has a trench formed at the surface. The microchip includes fluid circuits 4a and 5a formed by the trench and the surface of second substrate 6a facing the first substrate 100. The first substrate 100a has an air vent 2a connecting fluid circuits 4a and 5a to the outside of microchip, and in the vicinity of air vent 2a, has projections 1a and 3a on the surface of first substrate 100a, in fluid circuits 4a and 5a. The vicinity of air vent 2a may be set appropriately, and distance and the like are not specifically limited, as long as the operation as described later is caused. Projections 1a and 3a are not in contact with the second substrate 6a. It is necessary that a space between the second substrate 6a and the uppermost portion of the surface forming projections 1a and 3a in the thickness direction allows movement of the fluid. In the present embodiment, fluid circuits 4a and 5a serve as excess storages.

It is noted that, in the present embodiment, the distance D3 between the second substrate 6a and the upper surface in the thickness direction of projection 3a is larger than the distance D4 between the second substrate 6a and the upper surface in the thickness direction of projection 1a. The distance between air vent 2a to projection 1a is L2. Such a structure enables the fluid operation that will be described later.

Further, in the present embodiment, the surfaces forming projections 1a and 3a are inclined in the direction to the second substrate 6a. Here, "inclined in the direction to the second substrate 6a" means that the angle θ1a is smaller than 90°, for example. In the present embodiment, preferably, the angle θ1a is 30 to 89°, and more preferably, 45 to 87°. Such a range of angle θ1a is selected from the following reason. When the first substrate 100 is formed by injection molding, it is necessary that θ1<89°, considering releasing from a metal mold. If θ1<30°, the volume of projection itself becomes large, and hence, the projection itself would be a dead space.

In the present embodiment, both the surface forming the right side and the surface forming the left side of projections 1a and 3a of FIG. 4 are inclined. It is noted, however, that only the right side or left side surface may be inclined, or only one of the projections 1a and 3a may be inclined. Further, the shape of projections 1a and 3a is not specifically limited, and other than the one shown in FIG. 4, the projection may have the shape of a circular cone or a pyramid.

Figure 5A:
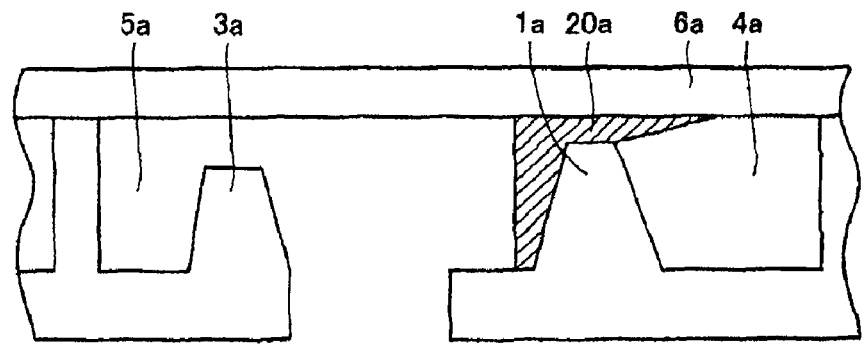
FIGS. 5A and 5B are schematic cross-sections representing a fluid operation in the microchip in accordance with the first embodiment.
Figure 5B:
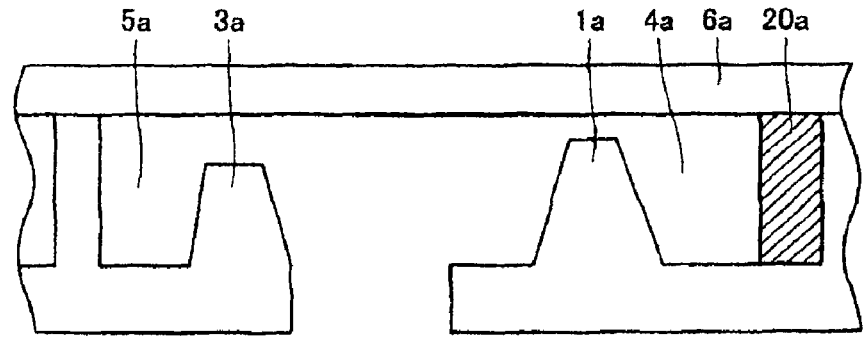

Next, the operation of fluid in the present embodiment will be described with reference to FIGS. 5A to 7B. First, as shown in FIGS. 5A and 5B, centrifugal force is applied in a direction to the right of the figure, so that fluid 20a moves from fluid circuit 5a to the surface forming projection 3a and to the surface forming projection 1a in this order. At this time, a first wall surface 8, an inner wall forming the through hole, and the surface forming projection 1 are inclined in the direction to the second substrate 6a and, therefore, the fluid can move smooth to the right side as shown in FIGS. 5A and 5B. Then, fluid 20a is introduced to fluid circuit 4a. After introduced to fluid circuit 4a, movement of fluid 20a is prevented by projection 1a unless centrifugal force is applied in the direction to the left side as will be described later, and therefore, the fluid is kept in fluid circuit 4a. Further, in the present embodiment, D3>D4 and, therefore, even if the flow of fluid 20a is prevented between the second substrate 6a and the upper surface in the thickness direction of projection 1a, fluid 20a is stored temporarily in the portion of distance L2 in the fluid circuit, as there is a distance L2 between air vent 2a to the projection 1a. Therefore, fluid 20a does not leak out through air vent 2a to the outside of the microchip.

Figure 6A:
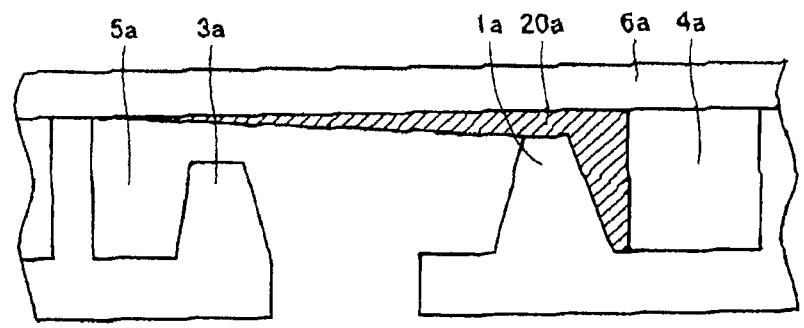
FIGS. 6A and 6B are schematic cross-sections representing a fluid operation in the microchip in accordance with the first embodiment.
Figure 6B:
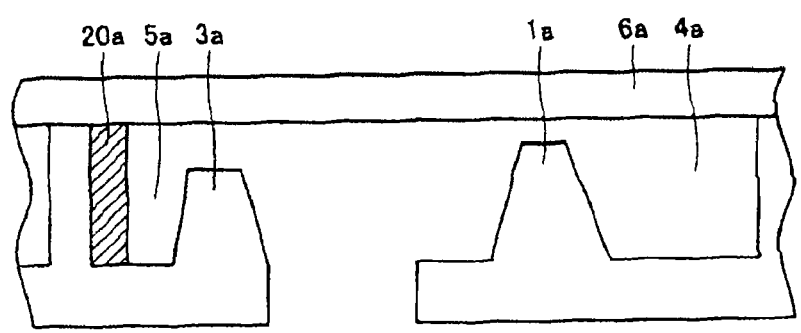

Next, as shown in FIGS. 6A and 6B, when the centrifugal force is applied in the direction to the left side of FIG. 6A, fluid 20a moves from fluid circuit 4a to fluid circuit 5a. At this time, fluid 20a passes through the space between the second substrate 6a and the upper surface in the thickness direction of projection 1a, and passes through the space between the second substrate 6a and the upper surface in the thickness direction of projection 3a, to move to fluid circuit 5a. As the projection 3a is inclined as described above, fluid 20a can move smooth to the fluid circuit 5a. After introduced to fluid circuit 5a, movement of fluid 20a is prevented by projection 3a unless centrifugal force is applied in the direction to the right side of the figure, and the fluid is kept in fluid circuit 5a. Further, in the present embodiment, D3>D4 and, therefore, flow of fluid 20a is not much hindered by the space between the second substrate 6a and the upper surface in the thickness direction of projection 3a. Therefore, it is unnecessary to provide the distance L2 between air vent 2a and projection 1a, in the vicinity of projection 3a, and hence, space can be saved.

Figure 7A:
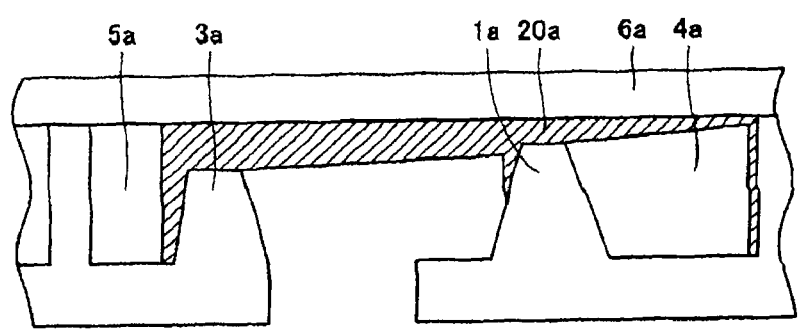
FIGS. 7A and 7B are schematic cross-sections representing a fluid operation in the microchip in accordance with the first embodiment.
Figure 7B:
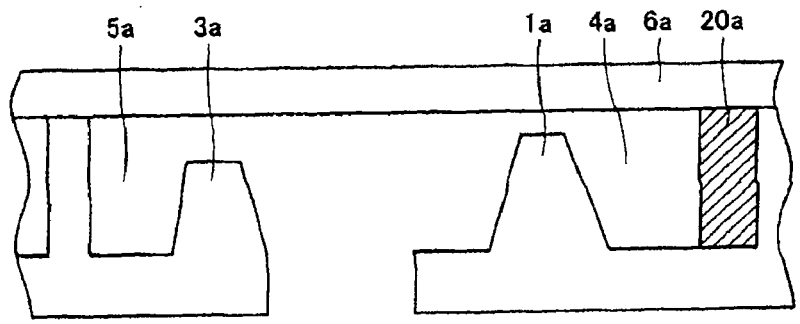

Next, as shown in FIGS. 7A and 7B, when centrifugal force is applied in the direction to the right side of the figure, fluid 20a moves from fluid circuit 5a to fluid circuit 4a. At this time, fluid 20a passes through the space between the second substrate 6a and the upper surface in the thickness direction of projection 3a and through the space between the second substrate 6a and the upper surface in the thickness direction of projection 1a, to the fluid circuit 4a. As the projection 1a is inclined as described above, fluid 20a can move smooth to the fluid circuit 4a. After introduced to fluid circuit 4, movement of fluid 20 is prevented by projection 1a unless centrifugal force is applied in the direction of arrow 22 mentioned above, and the fluid is kept in fluid circuit 4a.

As the above-described operations are repeated, it is possible to provide an air vent lower in the thickness direction than the excess storage and, as a result, the microchip can be reduced in size.

Second Embodiment

Figure 8:
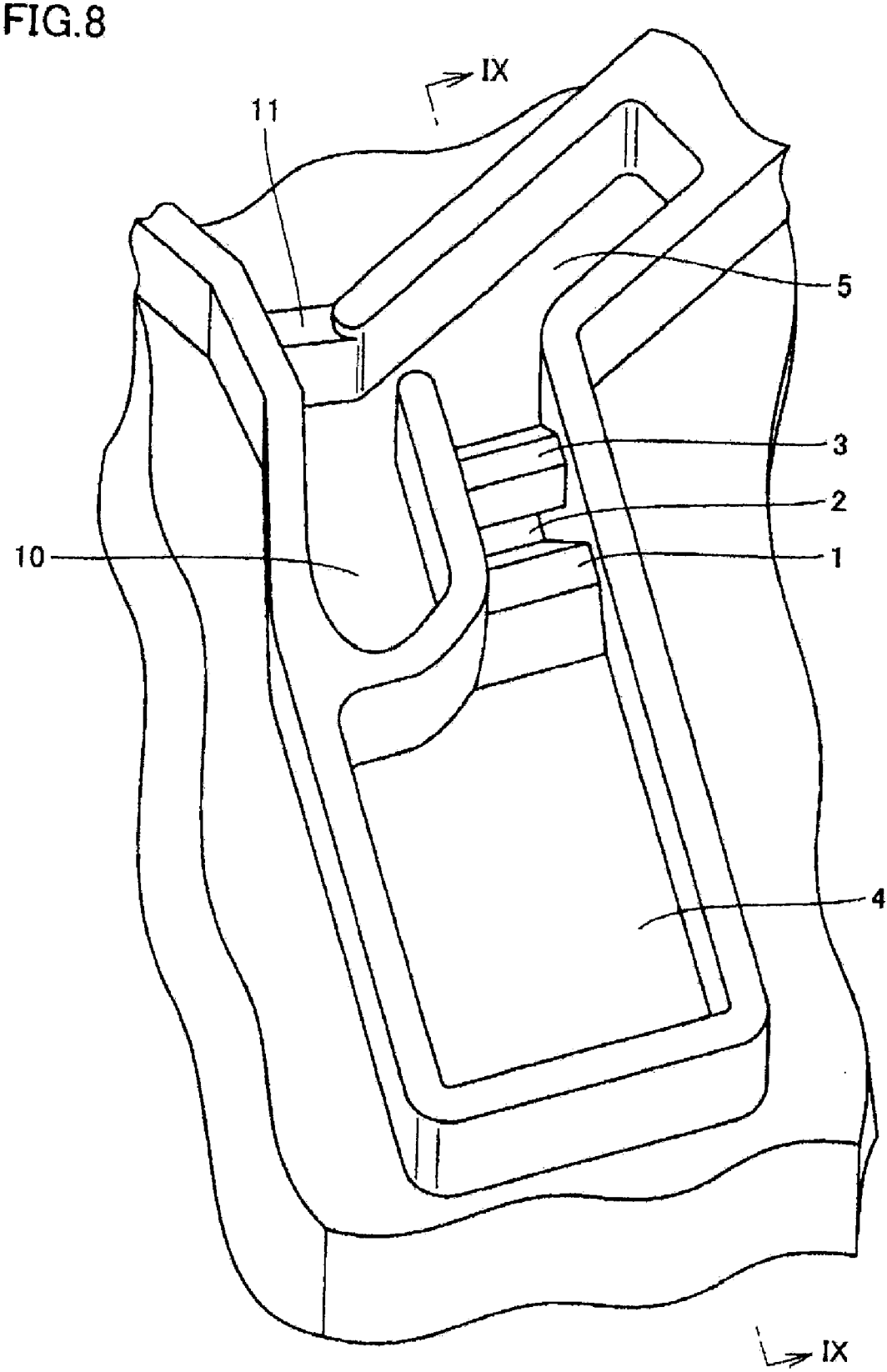
FIG. 8 is a perspective view of a portion of a microchip in accordance with a second embodiment.
Figure 9:
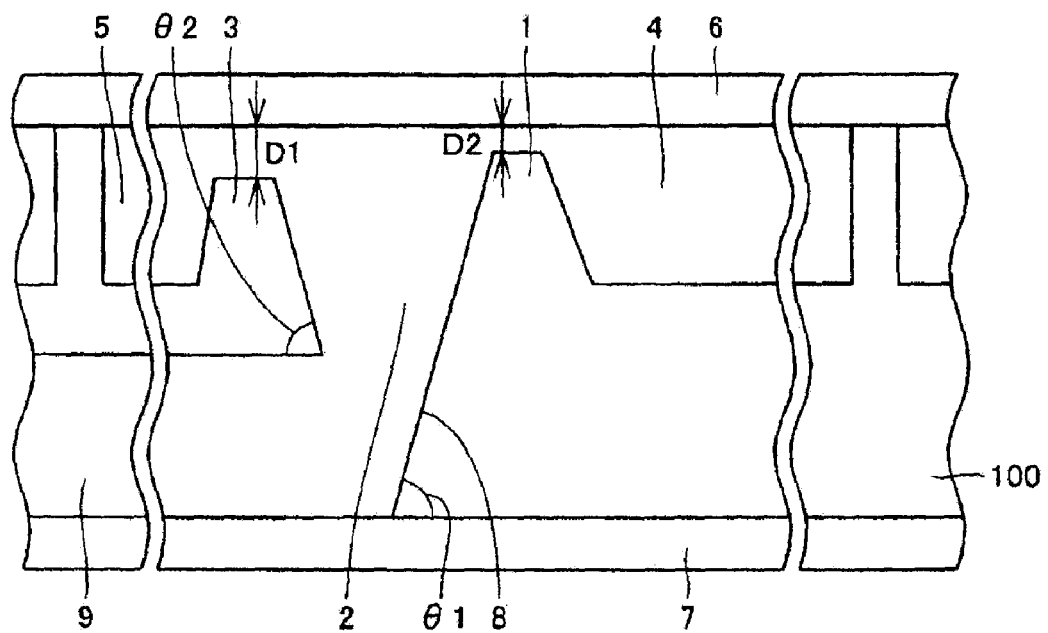
FIG. 9 is a cross-section taken along the line IX-IX of FIG. 8.

FIG. 8 is a perspective view of a portion of microchip in accordance with the present embodiment. FIG. 9 is a cross-section taken along the line IX-IX of FIG. 8. FIGS. 10A to 12B are schematic cross-sections showing the operation of fluid in the microchip in accordance with the present embodiment.

In the following, description will be given with reference to FIGS. 8 to 12B. In the present embodiment, "upper in the thickness direction" refers to the direction to the third substrate 6 in the thickness direction, and "lower in the thickness direction" refers to the direction to the second substrate 7 in the thickness direction.

First, a simple operation of the microchip will be described with reference to FIGS. 8 and 9. In the microchip, the fluid is introduced through flow path 11 by the application of centrifugal force, and a prescribed amount is measured by measuring section 10. Further, the fluid unnecessary for the detection by the microchip, that is, the so-called excess fluid, is introduced to the second fluid circuit 4.

Next, the structure of microchip will be described. The microchip in accordance with the present invention is formed by joining, in order, the second substrate 7, the first substrate 100 and the third substrate 6. In FIG. 8, the second substrate 7 and the third substrate 6 are omitted for convenience. The first substrate 100 has trenches formed on opposite surfaces. The microchip has a first fluid circuit 9 formed by the trench and the surface of second substrate 7 facing the first substrate 100, and the second fluid circuits 4 and 5 formed by the trench and the surface of third substrate 6 facing the first substrate 100. The first substrate 100 has a through hole 2 connecting the first fluid circuit 9 and the second fluid circuits 4 and 5, and in the vicinity of through hole 2, has projections 1 and 3 on the surface of first substrate, in the second fluid circuits 4 and 5. The vicinity of through hole 2 may be set appropriately, and distance and the like are not specifically limited, as long as the operation as described later is caused. Projections 1 and 3 are not in contact with the third substrate 6. It is necessary that a space between the third substrate 6 and the uppermost portions of the surface forming projections 1 and 3 in the thickness direction allows movement of the fluid. Further, in the present embodiment, the distance D1 between the third substrate 6 and the uppermost portion in the thickness direction of the surface forming projection 3 is larger than the distance D2 between the third substrate 6 and the uppermost portion in the thickness direction of the surface forming projection 1. Here, the second fluid circuits 4 and 5 of the present embodiment serve as excess storages. It is noted that the first substrate 100 may be a black substrate or a non-transparent substrate, while the second substrate 7 and the third substrate 6 may be transparent substrates.

The present embodiment further includes a first wall surface 8 that connects the surface of second substrate 7 forming the first fluid circuit 9 to the inner wall forming through hole 2, and shutting off the first fluid circuit 9. The first wall surface 8 shutting off the first fluid circuit 9 shuts off the space in which fluid can move in the first fluid circuit 9, and the fluid passing to the first wall surface 8 substantially proceeds in the direction to the wall surface forming the through hole 2. The first wall surface 8 and the inner wall forming through hole 2 are inclined in the direction to the third substrate 6. Here, "inclined in the direction to the third substrate 6" means that the angle θ1 formed by the first wall surface 8 and the second substrate 7 is smaller than 90°. In the present embodiment, preferably, the angle θ1 is 30 to 89°, and more preferably, 45 to 87°. Such a range of angle θ1 is derived from the viewpoint that the following operation is done smooth. When the first substrate 100 is formed by injection molding, it is necessary that θ1<89°, considering releasing from a metal mold. If θ1<30°, the volume of projection itself becomes large, and hence, the projection itself would be a dead space.

In the present embodiment, the surfaces forming projections 1 and 3 are inclined in the direction to the third substrate 6. As described above, "inclined in the direction to the third substrate 6" means that, for example, the angle θ2 is smaller than 90°. In the present embodiment, preferably, the angle θ2 is 30 to 89°, and more preferably, 45 to 87°. Such a range of angle θ2 is selected from the same reason as for the angle θ1 described above. The range of angle θ2 is derived from the viewpoint that the following operation is done smooth. Further, in the present embodiment, both the surface forming the right side and the surface forming the left side of projections 1 and 3 of FIG. 9 are inclined. It is noted, however, that only the right side or left side surface may be inclined, or only one of the projections 1 and 3 may be inclined. Further, the shape of projections 1 and 3 is not specifically limited, and other than the one shown in FIG. 9, the projection may have the shape of a circular cone or a pyramid. In the present embodiment, the first wall surface 8, the inner wall forming through hole 2 and the surface forming projection 1 have such a relation that these can be connected by one line. The shape, however, is not specifically limited, provided that the first wall surface 8, the inner wall forming through hole 2 and the surface forming projection 1 are inclined in the direction to the third substrate 6. Therefore, it may be possible that the first wall surface 8, the inner wall forming through hole 2 and the surface forming projection 1 are not in the relation that these can be connected by one line but formed stepwise, or at least one of the surface forming projection 1, the inner wall forming through hole 2 and the first wall surface 8 may be inclined in the direction to the third substrate 6.

Figure 10A:
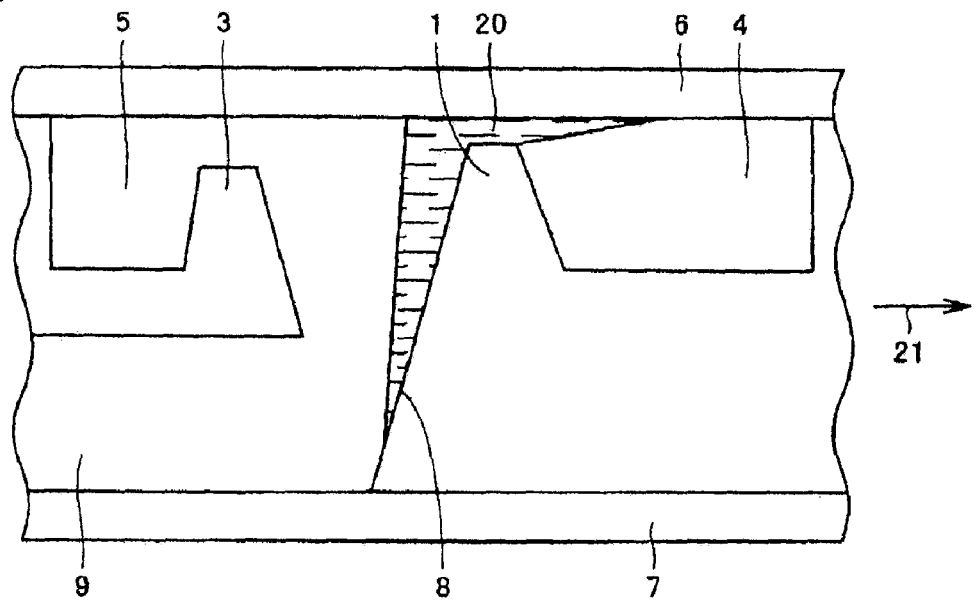
FIGS. 10A and 10B are schematic cross-sections representing a fluid operation in the microchip in accordance with the second embodiment.
Figure 10B:
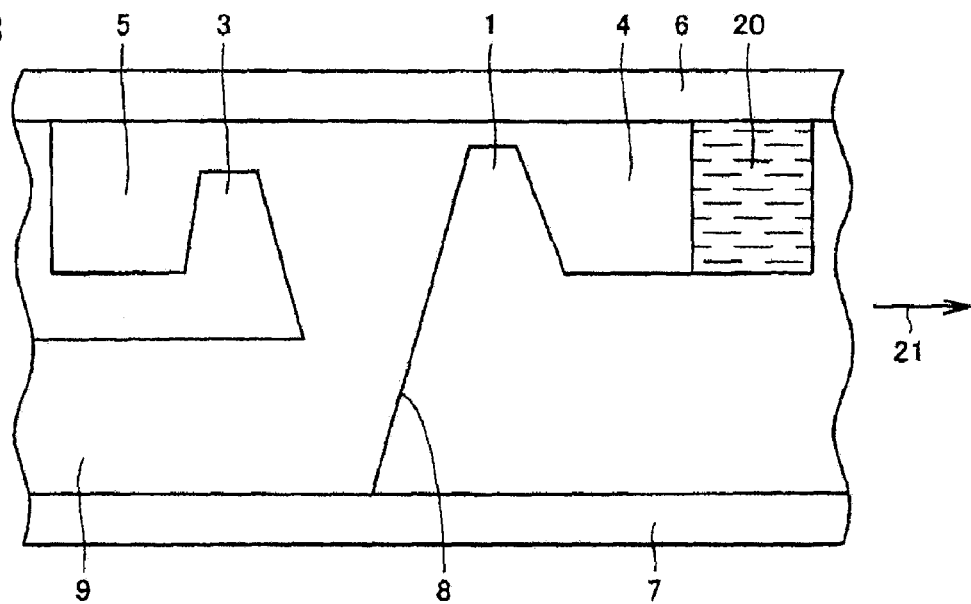

Next, the operation of fluid in the present embodiment will be described with reference to FIGS. 10A to 12B. First, as shown in FIGS. 10A and 10B, centrifugal force is applied in the direction of an arrow 21, so that fluid 20 moves from the first fluid circuit 9 and the second fluid circuit 5 to the first wall surface 8, the inner wall forming the through hole, and to the surface forming projection 1, in this order. At this time, the first wall surface 8, the inner wall forming the through hole and the surface forming projection 1 are inclined in the direction to the third substrate 6 and, therefore, the fluid can move smooth in the direction of arrow 21, as shown in FIGS. 10A and 10B. Then, fluid 20 is introduced to the second fluid circuit 4. After introduced to the second fluid circuit 4, movement of fluid 20 is prevented by projection 1 unless centrifugal force is applied in the direction of arrow 22 as will be described later, and the fluid is kept in the second fluid circuit 4.

Figure 11A:
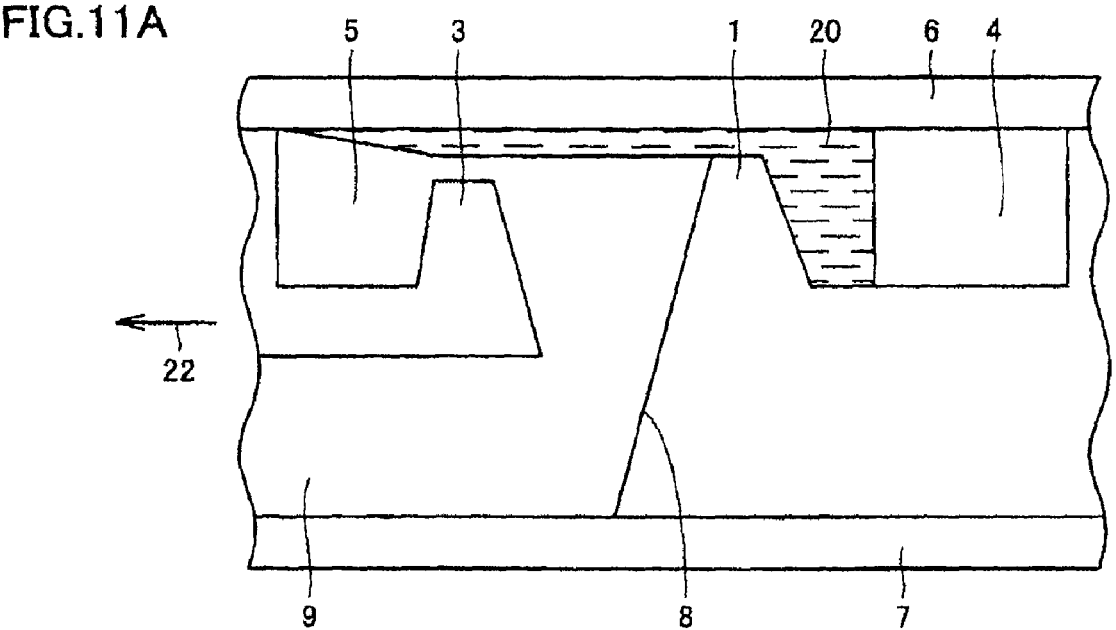
FIGS. 11A and 11B are schematic cross-sections representing a fluid operation in the microchip in accordance with the second embodiment.
Figure 11B:
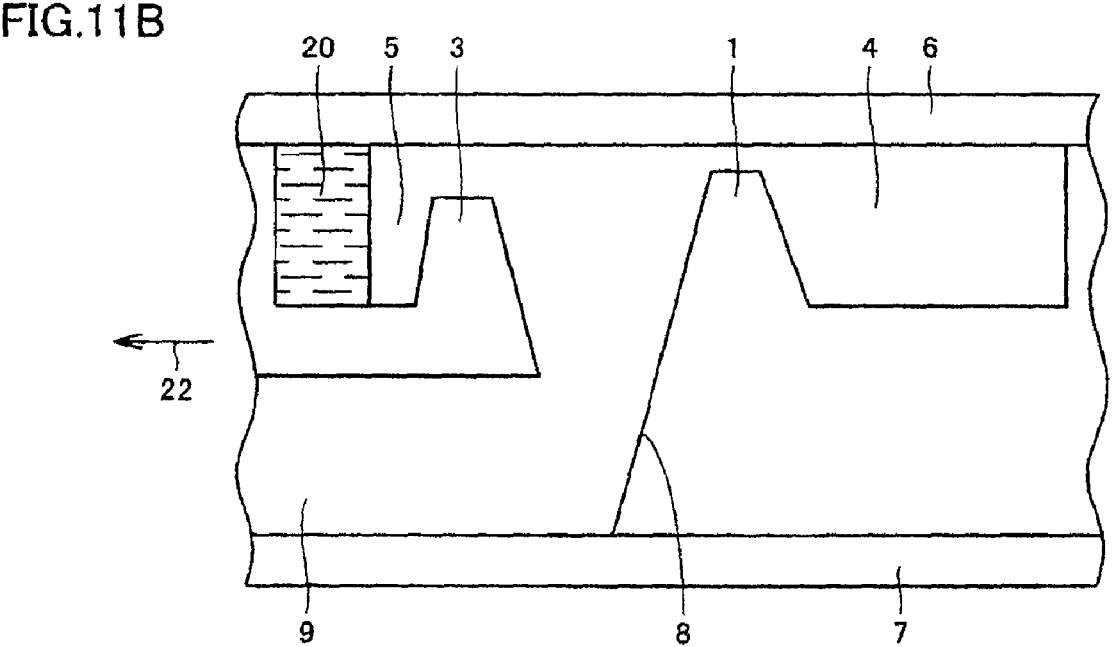

Next, as shown in FIGS. 11A and 11B, when centrifugal force is applied in the direction of arrow 22, fluid 20 moves from the second fluid circuit 4 to the second fluid circuit 5. At this time, fluid 20 passes through the space between the third substrate 6 and the upper surface in the thickness direction of projection 1, and through the space between the third substrate 6 and the upper surface in the thickness direction of projection 3, and moves to the second fluid circuit 5. Projection 3 is inclined as described above and D1>D2, so that when centrifugal force is applied in the direction of arrow 22, fluid 20 can move smooth to the second fluid circuit 5, and the flow of fluid to fluid circuit 9 can be prevented. After introduced to the second fluid circuit 5, movement of fluid 20 is prevented by projection 3 unless centrifugal force is applied in the direction of arrow 23 as will be described later, and the fluid is kept in the second fluid circuit 5.

Figure 12A:
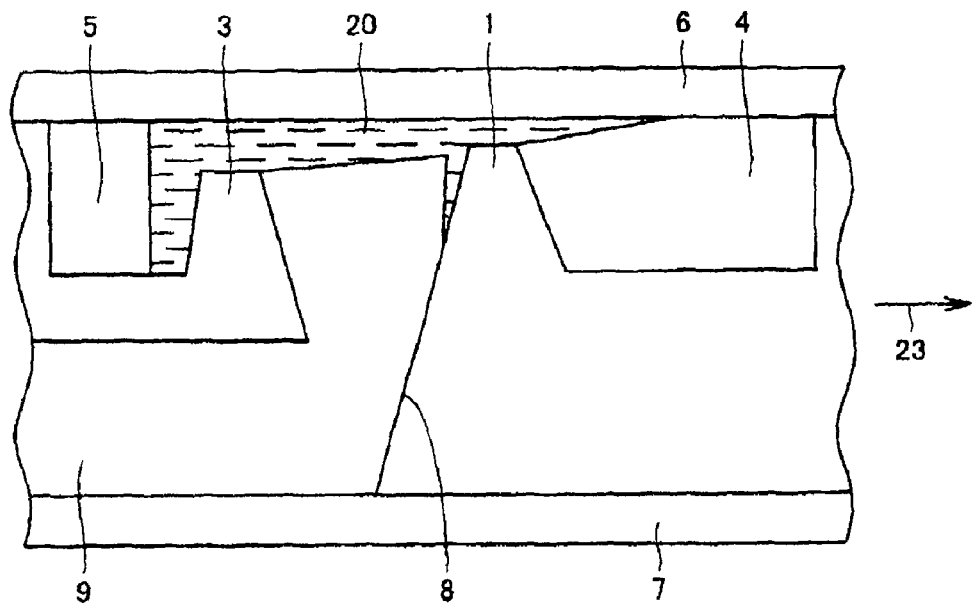
FIGS. 12A and 12B are schematic cross-sections representing a fluid operation in the microchip in accordance with the second embodiment.
Figure 12B:
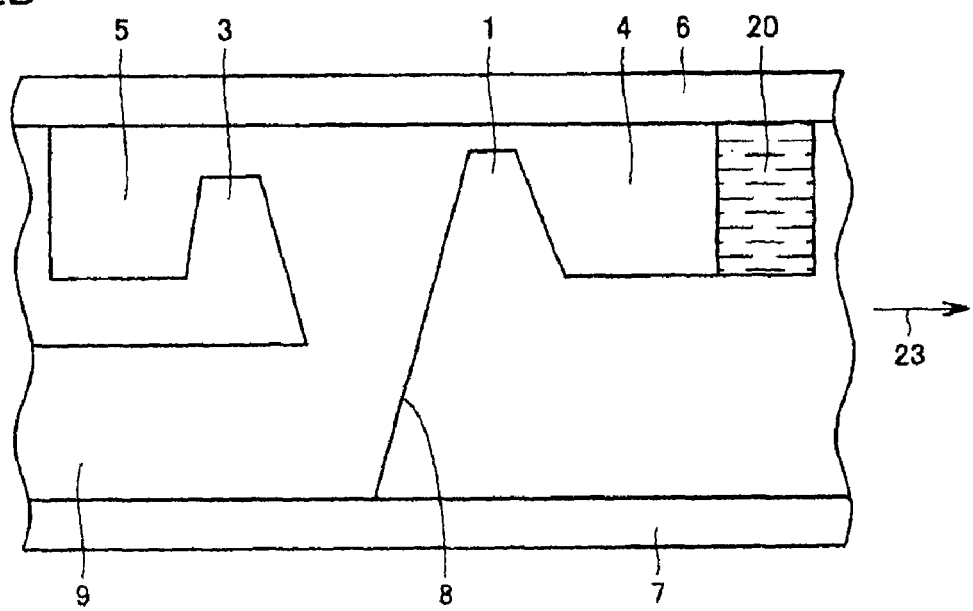

Next, as shown in FIGS. 12A and 12B, when centrifugal force is applied in the direction of an arrow 23, fluid 20 moves from the second fluid circuit 5 to the second fluid circuit 4. At this time, fluid 20 passes through the space between the third substrate 6 and the upper surface in the thickness direction of projection 3 and through the space between the third substrate 6 and the upper surface in the thickness direction of projection 1, and moves to the second fluid circuit 4. At this time, since D1>D2, fluid 20 is temporarily kept on the wall surface on the left side forming the projection 1. The wall surface, however, is inclined as described above and, therefore, when centrifugal force is applied in the direction of arrow 23, fluid 20 moves smooth to the second fluid circuit 4. After introduced to the second fluid circuit 4, movement of fluid 20 is prevented by projection 1 unless centrifugal force is applied in the direction of arrow 22 as described above, and the fluid is kept in the second fluid circuit 4.

As the above-described operations are repeated, the fluid 20 as the excess fluid once introduced to the second fluid circuit 4 never flows back to the first fluid circuit 9. Therefore, the fluid as the excess fluid can be stored in the second fluid circuits 4 and 5 that are positioned upper in the thickness direction than first fluid circuit 9, and as a result, microchip can be reduced in size.

Third Embodiment

Figure 13:
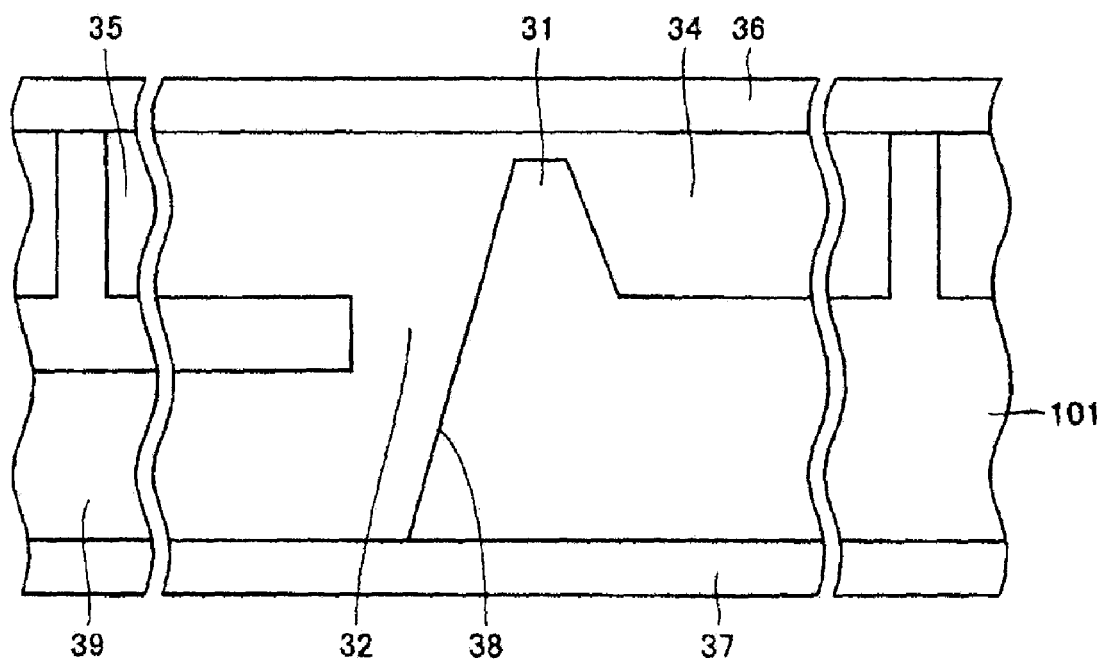
FIG. 13 is a schematic cross-section of a portion of a microchip in accordance with a third embodiment.

FIG. 13 is a schematic cross-section of a portion of the microchip in accordance with the present embodiment. In the present embodiment, "upper in the thickness direction" refers to the direction to the third substrate 36 in the thickness direction, and "lower in the thickness direction" refers to the direction to the second substrate 37 in the thickness direction.

In the following, description will be given with reference to FIG. 13. The present embodiment is the same as the first embodiment except that only one projection 31 is formed. Specifically, the microchip in accordance with the present embodiment is formed by joining a second substrate 37, a first substrate 101 and a third substrate 36 in this order. The first substrate 101 has trenches formed on opposite surfaces. The microchip includes a first fluid circuit 39 formed by the trench and the surface of second substrate 37 facing the first substrate 101, and second fluid circuits 34 and 35 formed by the trenches and the surface of the third substrate 36 facing the first substrate 101. The first substrate 101 has a through hole 32 connecting the first fluid circuit 39 to the second fluid circuits 34 and 35, and has a projection 31 in the vicinity of through hole 32 on the surface of the first substrate in second fluid circuits 34 and 35. The vicinity of through hole 32 may be set appropriately, and distance and the like are not specifically limited, as long as the operation as described later is caused. Projection 31 is not in contact with the third substrate 6, and it is necessary that a space between the third substrate 36 and the uppermost portion of the surface forming projection 31 in the thickness direction allows movement of the fluid. Specifically, the length in the thickness direction of microchip is smaller than the length in the thickness direction of second fluid circuits 34 and 35. In the present embodiment, fluid circuits 34 and 35 serve as excess storages.

The operation of fluid in the present embodiment is the same as that of FIGS. 10A and 10B. When centrifugal force is applied in the direction to the left of FIG. 13, as there is only one projection 31 in the present embodiment, it is preferred that centrifugal force in the direction to the left of FIG. 13 is continuously applied even after the fluid has moved to the second fluid circuit 35. When centrifugal force is applied in the direction to the right of FIG. 13, fluid 20 moves from the second fluid circuit 35 to the second fluid circuit 34. At this time, fluid 20 passes through the space between the third substrate 36 and the upper surface in the thickness direction of projection 31, and moves to the second fluid circuit 34. As the projection is inclined as described above, fluid 20 can move smooth to the second fluid circuit 34. After introduced to the second fluid circuit 34, movement of fluid 20 is prevented by projection 31, and the fluid is kept in the second fluid circuit 34.

As the above-described operations are repeated, the fluid 20 as the excess fluid once introduced to the second fluid circuit 34 never flows back to the first fluid circuit 39. Therefore, the fluid as the excess fluid can be stored in the second fluid circuits 34 and 35 that are positioned upper in the thickness direction than first fluid circuit 39, and as a result, microchip can be reduced in size.

Fourth Embodiment

Figure 14:
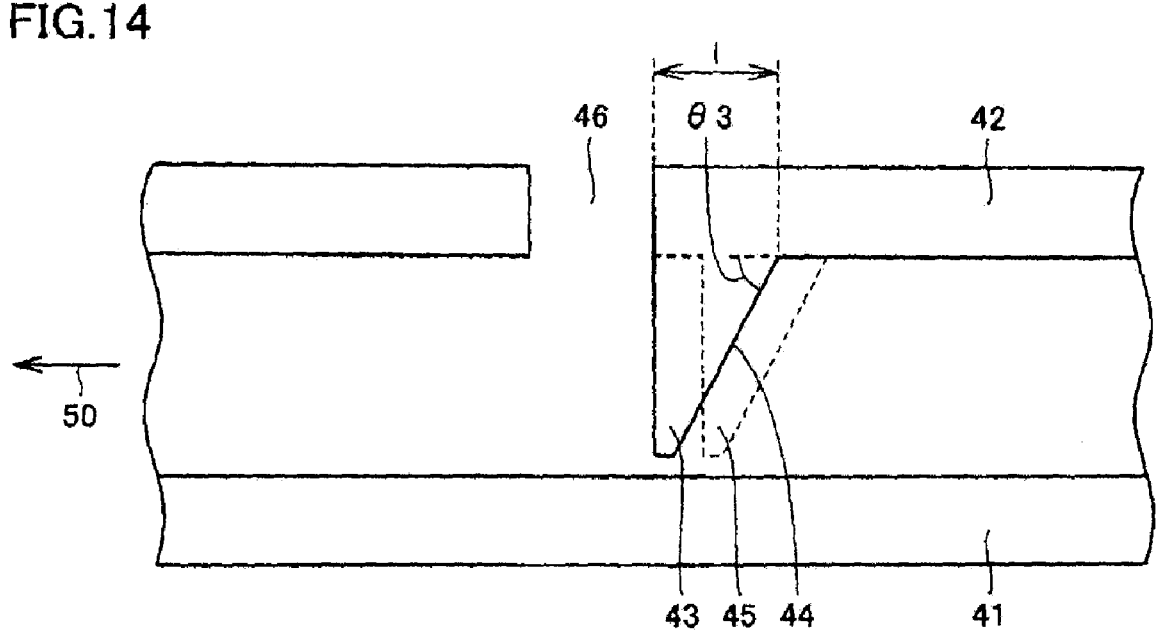
FIG. 14 is a schematic cross-section of a portion of a microchip in accordance with a fourth embodiment.

FIG. 14 is a schematic cross-section of a portion of the microchip in accordance with the present embodiment. In the present embodiment, "upper in the thickness direction" refers to the direction to the second substrate 42 in the thickness direction, and "lower in the thickness direction" refers to the direction to the first substrate 41 in the thickness direction.

Next, description will be given with reference to FIG. 14. First, the structure of microchip in accordance with the present embodiment will be described. The microchip of the present embodiment is formed by joining a first substrate 41 having a trench formed on the substrate surface with a second substrate 42. The microchip includes a fluid circuit formed by the trench and the surface of the second substrate 42 facing the first substrate 41. The second substrate 42 has an air vent 46 connecting the fluid circuit to the outside of the microchip, and has a projection 43 in the vicinity of air vent 46, on the surface of second substrate 42 in the fluid circuit. The vicinity of air vent 46 may be set appropriately, and distance and the like are not specifically limited, as long as the operation as described later is caused. By way of example, projections 45 formed as dots may be provided. Further, in the present embodiment, the projection 43 is formed on the upstream side of fluid operation when the fluid moves in the direction of an arrow 50, as will be described later. Projection 43 is not in contact with the first substrate 41, and it is necessary that the space between the first substrate 41 and the lowermost portion in the thickness direction of the surface forming projection 43 allows movement of the fluid. Specifically, the length of projection 43 in the thickness direction of microchip is smaller than the length in the thickness direction of the fluid circuit.

In the present embodiment, the surface forming projection 43 is inclined in the direction to the first substrate 41. Particularly, it is preferred that the surface 44 on the right side of FIG. 14, that is, the upstream side of fluid operation mentioned above, forming projection 43 is inclined. Here, "inclined in the direction to the first substrate 41" specifically means that the angle θ3 formed by the surface 44 and the surface of second substrate 42 on the side of fluid circuit is smaller than 90°. In the present embodiment, preferably, the angle θ3 is 30 to 89°, and more preferably, 45 to 87°. Such a range of angle θ3 is derived from the viewpoint that the following operation is done smooth. Further, surface 44 is inclined sufficiently so that fluid will not be left thereon, and as the length 1 in FIG. 14 is made longer, reduction in volume of flow path on the upstream side of the fluid resulting from the increased volume of projection 43 can be prevented.

Next, the operation of fluid in the present embodiment will be described. In the present embodiment, the fluid moves in the fluid circuit in the direction of an arrow 50. At the same time, air in the space not filled with the fluid in the fluid circuit also moves in the direction of arrow 50. It follows that the fluid moves passing through the space between the first substrate 41 and the lower surface in the thickness direction of projection 43. By way of example, when centrifugal force is applied in the direction of arrow 50 and fluid is moved in the direction of arrow 50, the fluid moves smooth along the surface 44 to the space between the first substrate 41 and the lower surface in the thickness direction of projection 43. The fluid moves less smooth through the space between the first substrate 41 and the lower surface in the thickness direction of projection 43 as compared with other fluid circuits, and therefore, there is a pressure between the first substrate 41 and the lower surface in the thickness direction of projection 43. Further, because of projection 43, movement of fluid in the direction to air vent 46 is blocked. The fluid that escaped from the space between the first substrate 41 and the lower surface in the thickness direction of projection 43 proceeds in the direction of arrow 50 swiftly, and the operation is designed such that the fluid does not leak out through air vent 46 to the outside of microchip.

By such a shape, it becomes possible to provide air vent 46 at a position immediately above the fluid in operation, in the thickness direction. Provision of an air vent at such a position has been avoided, as there is a possibility of contact between the air vent and the fluid. As the air vent 46 is provided at a position immediately above the fluid in operation in the thickness direction, the position for air vent in the microchip not considered in the conventional examples becomes available and, as a result, microchip can be reduced in size.

In the present embodiment, it is also possible to provide a trench on that surface of first substrate 41 which is opposite to the surface to be joined to the second substrate 42, and to join this surface to a third substrate.

Fifth Embodiment

Figure 15:
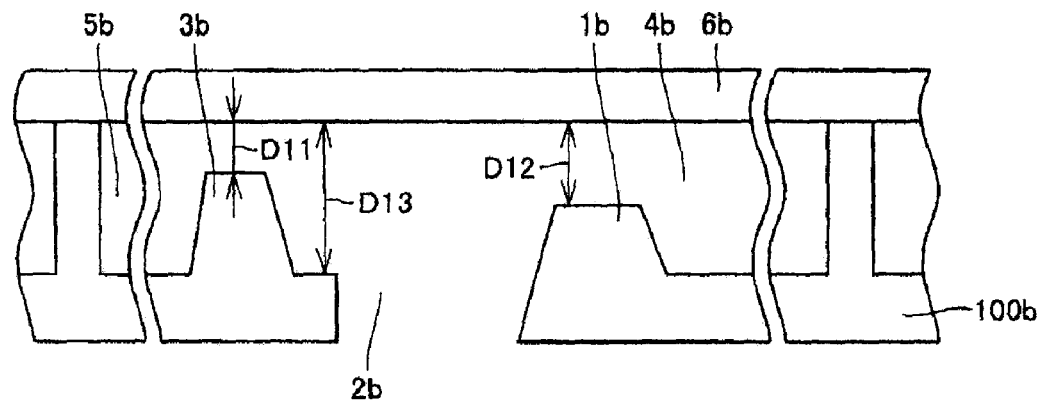
FIG. 15 is a cross-section of a microchip in accordance with a fifth embodiment.

FIG. 15 is a cross-sectional view showing another form of a microchip in accordance with an embodiment. FIGS. 16A to 17B are schematic cross-sections showing a fluid operation in the microchip in accordance with the present embodiment. Specifically, the present embodiment represents a modification of the first embodiment.

In the following, description will be given with reference to FIGS. 15 to 17B. In the present embodiment, "upper in the thickness direction" refers to the direction to the second substrate 6b in the thickness direction, and "lower in the thickness direction" refers to the direction to the first substrate 100b in the thickness direction.

The second substrate 6b, the first substrate 100b, fluid circuits 4b and 5b, air vent 2b and projections 1b and 3b are of the same shape as those in the first embodiment.

It is noted, however, that the distance D11 between the second substrate 6b and the upper surface in the thickness direction of projection 3b is smaller than the distance D12 between the second substrate 6b and the upper surface in the thickness direction of projection 1b. There is a distance between air vent 2b to projection 3b. Further, the distance D13 between the first substrate 6b and the upper surface in the thickness direction of first substrate 100b in FIG. 15 satisfies the relation of D13>D12>D11. Such a structure leads to the fluid operation as described below.

Further, the angle of inclination, shape and the like of projections 1b and 3b can appropriately be selected as in the first embodiment.

Figure 16A:
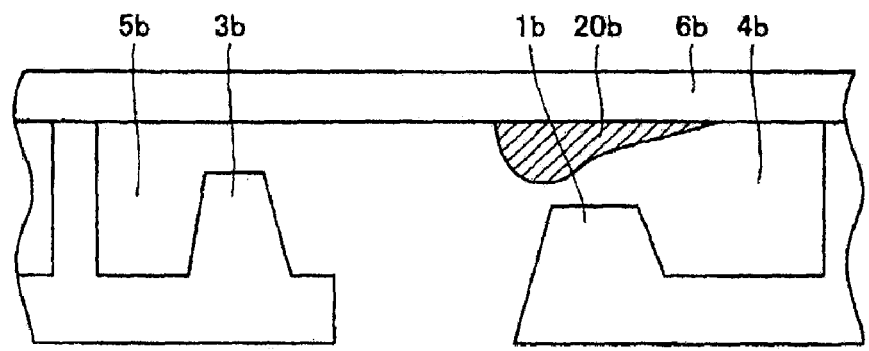
FIGS. 16A and 16B are schematic cross-sections representing a fluid operation in the microchip in accordance with the fifth embodiment.
Figure 16B:
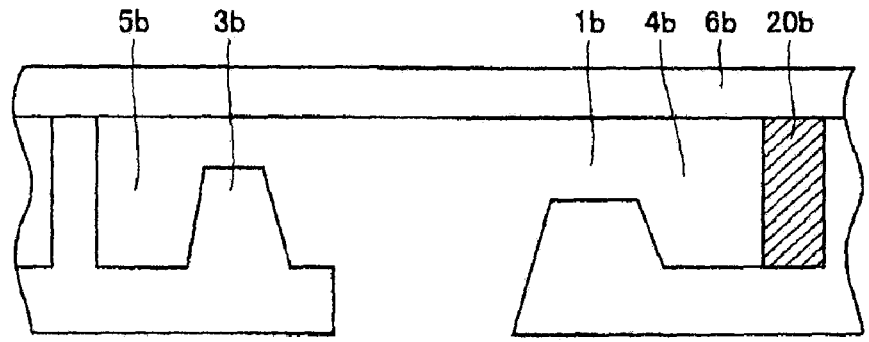

Next, the operation of fluid in the present embodiment will be described with reference to FIGS. 16A to 17B. First, as shown in FIGS. 16A and 16B, when centrifugal force is applied in the direction to the right of the figures, fluid 20b moves from fluid circuit 5b to the surface forming projection 3b and to the surface forming projection 1b, in this order. As shown in FIGS. 16A and 16B, the fluid can move smooth to the right. Then, fluid 20b is introduced to fluid circuit 4b. After introduced to fluid circuit 4b, movement of fluid 20b is prevented by projection 1b unless centrifugal force is applied in the direction to the left side as will be described later, and therefore, the fluid is kept in fluid circuit 4b.

Figure 17A:
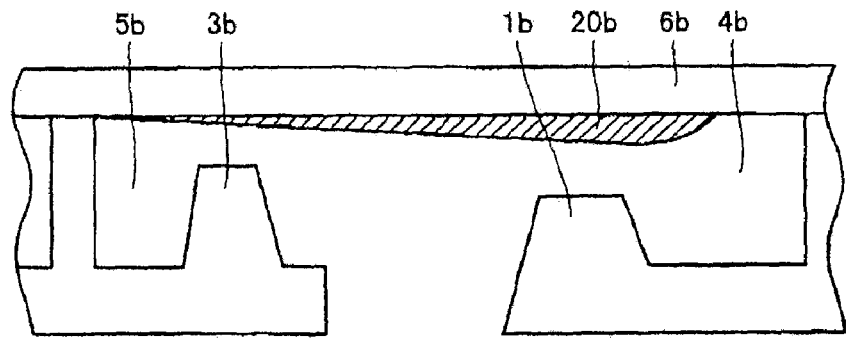
FIGS. 17A and 17B are schematic cross-sections representing a fluid operation in the microchip in accordance with the fifth embodiment.
Figure 17B:
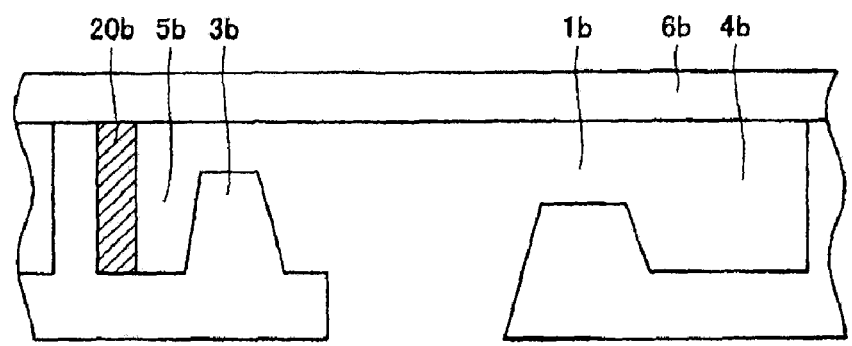

Next, as shown in FIGS. 17A and 17B, when centrifugal force is applied in the direction to the left of FIG. 17A, fluid 20b moves from fluid circuit 4b to fluid circuit 5b. At this time, fluid 20b passes through the space between the second substrate 6b and the upper surface in the thickness direction of projection 1b, and through the space between the second substrate 6b and the upper surface in the thickness direction of projection 3b, to the fluid circuit 5b. As the projection 3b is inclined as described above, fluid 20b can move smooth to fluid circuit 5b. After introduced to fluid circuit 5b, movement of fluid 20b is prevented by projection 3b unless centrifugal force is applied in the direction to the right side in the figure, and therefore, the fluid is kept in fluid circuit 5b. From the foregoing, it is unnecessary to ensure the length L2 between air vent 2b to projection 1b in the vicinity of projection 3b and, therefore, the space can be made smaller.

As the above-described operations are repeated, it is possible to provide an air vent lower in the thickness direction than the excess storage and, as a result, the microchip can be reduced in size.

Sixth Embodiment

Figure 18:
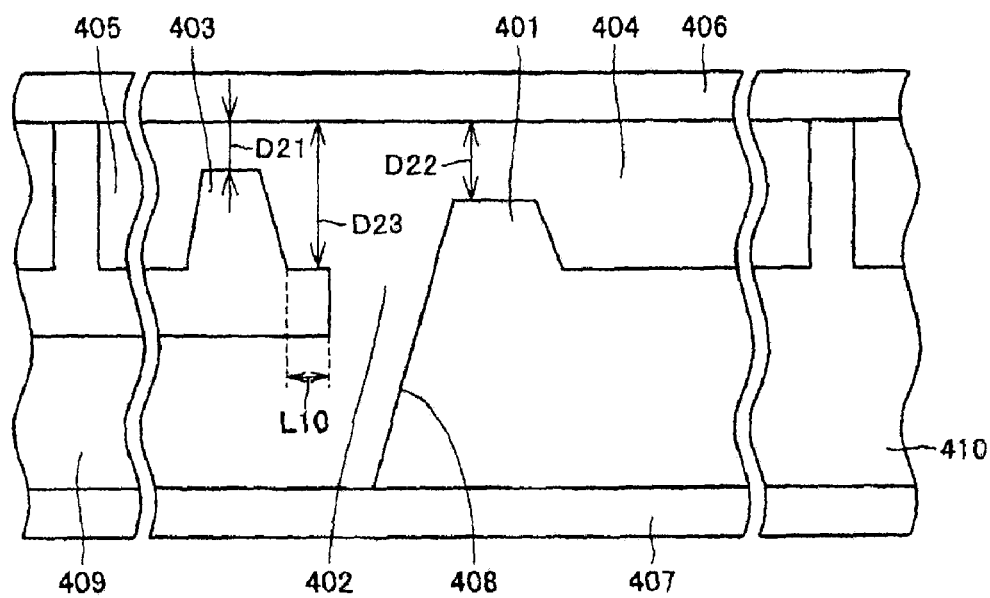
FIG. 18 is a cross-section of a microchip in accordance with a sixth embodiment.

FIG. 18 is a cross-section showing another form of the microchip in accordance with an embodiment. FIGS. 19A to 20B are schematic cross-sections showing a fluid operation in the microchip in accordance with the present embodiment. Specifically, the present embodiment represents a modification of the second embodiment.

In the following, description will be given with reference to FIGS. 18 to 20B. In the present embodiment, "upper in the thickness direction" refers to the direction to the third substrate 406 in the thickness direction, and "lower in the thickness direction" refers to the direction to the second substrate 407 in the thickness direction.

The second substrate 407, the first substrate 410, the third substrate 406, the first fluid circuit 409, the second fluid circuits 404 and 405, through hole 402 and projections 401 and 403 are of the same shape as those in the second embodiment.

It is noted, however, that the distance D21 between the third substrate 406 and the uppermost portion in the thickness direction of the surface forming projection 403 is smaller than the distance D22 between the third substrate 406 and the uppermost portion in the thickness direction of the surface forming projection 401. Further, the distance D23 between the first substrate 410 and the upper surface in the thickness direction of the third substrate 406 in FIG. 18 satisfies the relation of D23>D22>D21. Such a structure leads to the fluid operation as described below.

In the present embodiment, the second fluid circuits 404 and 405 serve as excess storages. It is noted that the first substrate 410 may be a black substrate or a non-transparent substrate, while the second substrate 407 and the third substrate 406 may be transparent substrates.

Further, the angle of inclination, shape and the like of projections 401 and 403 can appropriately be selected as in the second embodiment.

Figure 19A:
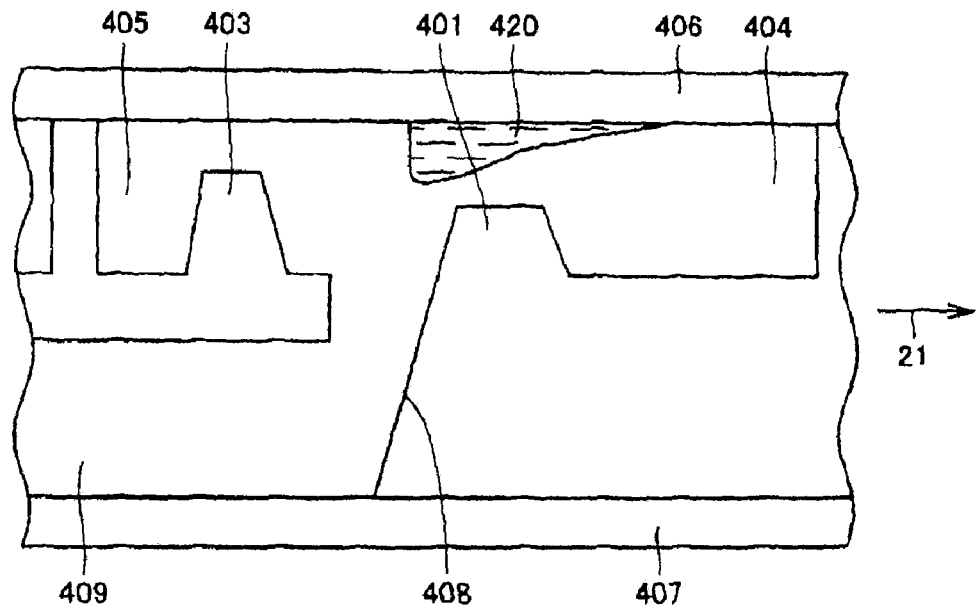
FIGS. 19A and 19B are schematic cross-sections representing a fluid operation in the microchip in accordance with the sixth embodiment.
Figure 19B:
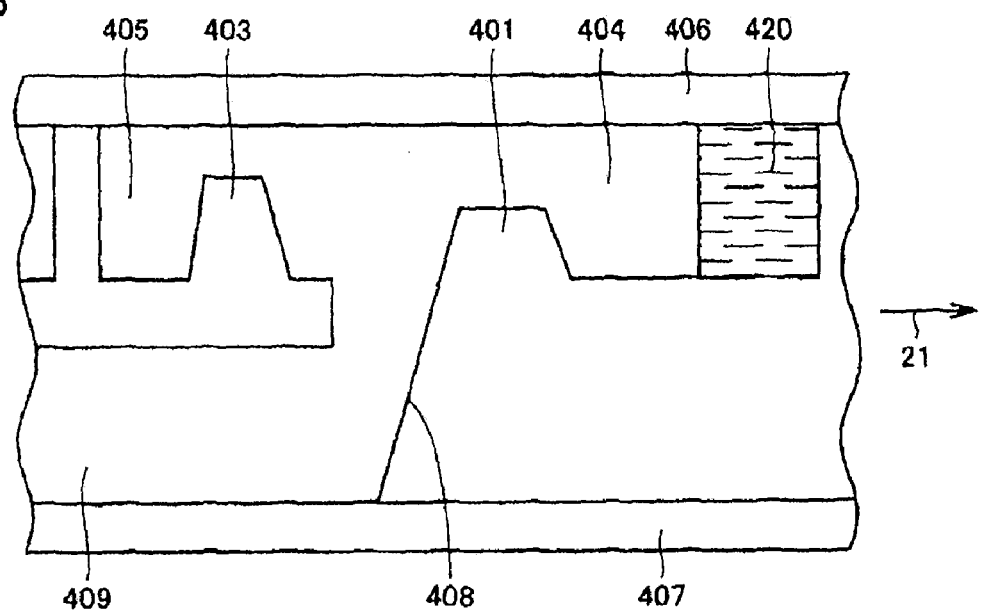

Next, the operation of fluid in the present embodiment will be described with reference to FIGS. 19A to 20B. First, as shown in FIGS. 19A and 19B, centrifugal force is applied in the direction of an arrow 21, so that fluid 20 moves from the first fluid circuit 409 to the first wall surface 408, the inner wall forming the through hole, and to the surface forming projection 1, in this order. At this time, as the first wall surface 8, the inner wall forming the through hole and the surface forming projection 401 are inclined in the direction to the third substrate 406, so that the fluid can move smooth in the direction of arrow 21 as shown in FIGS. 19A and 19B. Then, fluid 420 is introduced to the second fluid circuit 404. After introduced to the second fluid circuit 404, movement of fluid 420 is prevented by projection 401 unless centrifugal force is applied in the direction of arrow 22 as will be described later, and the fluid is kept in the second fluid circuit 4.

Figure 20A:
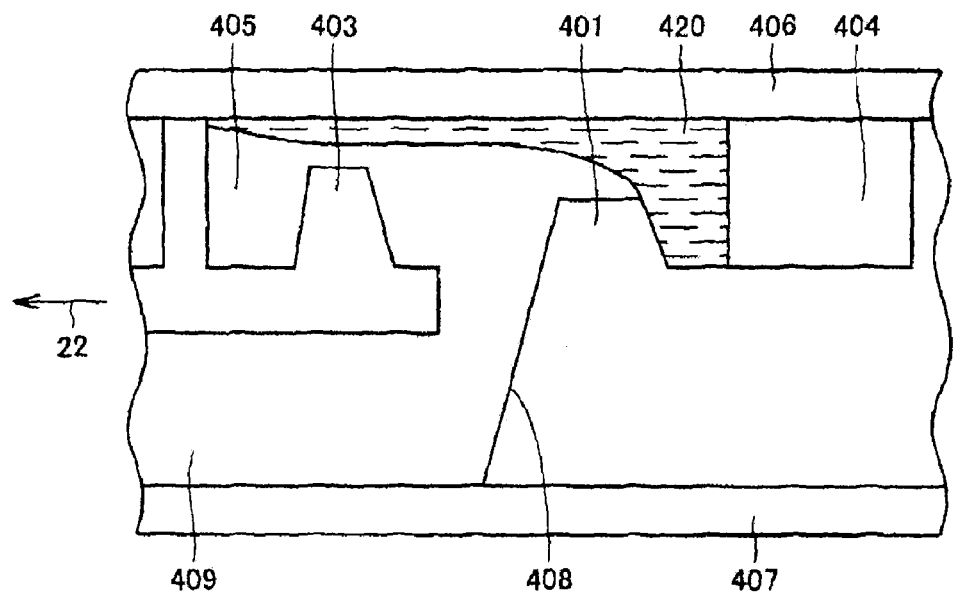
FIGS. 20A and 20B are schematic cross-sections representing a fluid operation in the microchip in accordance with the sixth embodiment.
Figure 20B:
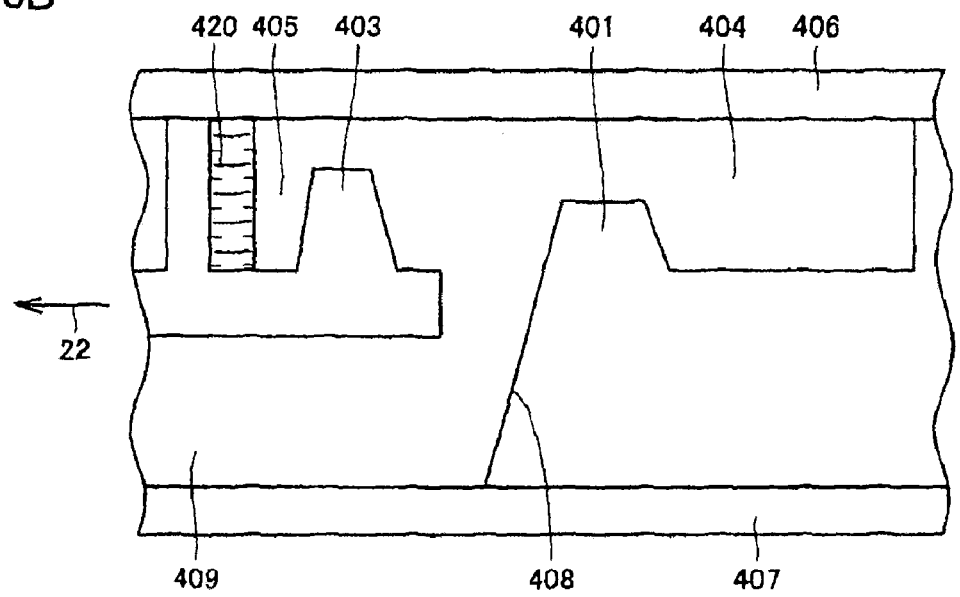

Next, as shown in FIGS. 20A and 20B, when centrifugal force is applied in the direction of arrow 22, fluid 420 moves from the second fluid circuit 404 to the second fluid circuit 405. At this time, fluid 20 passes through the space between the third substrate 406 and the upper surface in the thickness direction of projection 401, and through the space between the third substrate 406 and the upper surface in the thickness direction of projection 403, and moves to the second fluid circuit 405. As described above, projection 403 is inclined and has a flat portion of distance L10. Therefore, when centrifugal force is applied in the direction of arrow 22, fluid 420 is temporarily kept at the flat portion of distance L10, and moves smooth to the second fluid circuit 405. After introduced to the second fluid circuit 405, movement of fluid 420 is prevented by projection 403 unless centrifugal force is applied in the direction of arrow 21 described above, and therefore, the fluid is kept in the second fluid circuit 405.

As the above-described operations are repeated, the fluid 420 as the excess fluid once introduced to the second fluid circuit 404 never flows back to the first fluid circuit 409. Therefore, the fluid as the excess fluid can be stored in the second fluid circuits 404 and 405 that are positioned upper in the thickness direction than first fluid circuit 409, and as a result, microchip can be reduced in size.

Seventh Embodiment

Figure 21:
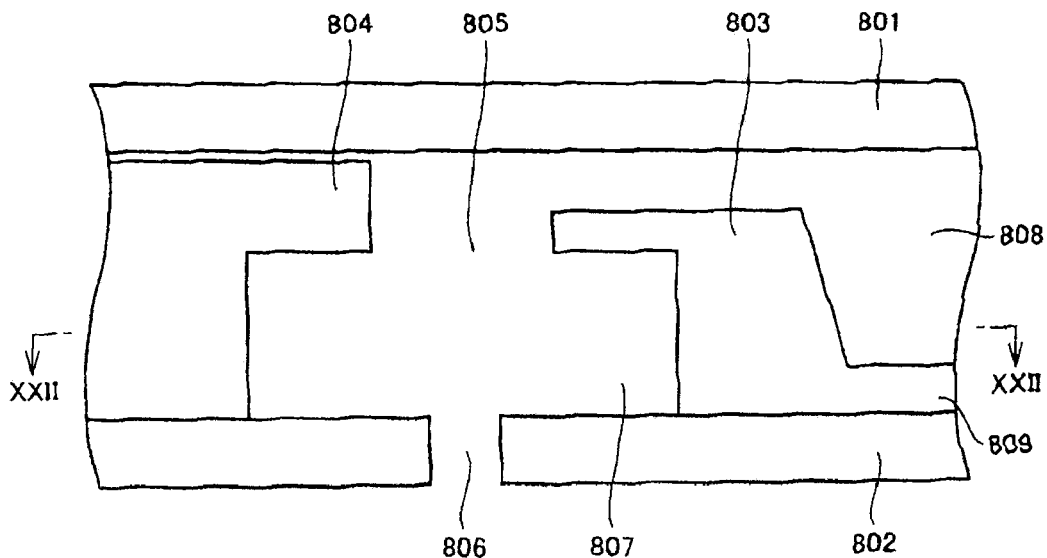
FIG. 21 is a cross-section of a microchip in accordance with a seventh embodiment.
Figure 22:
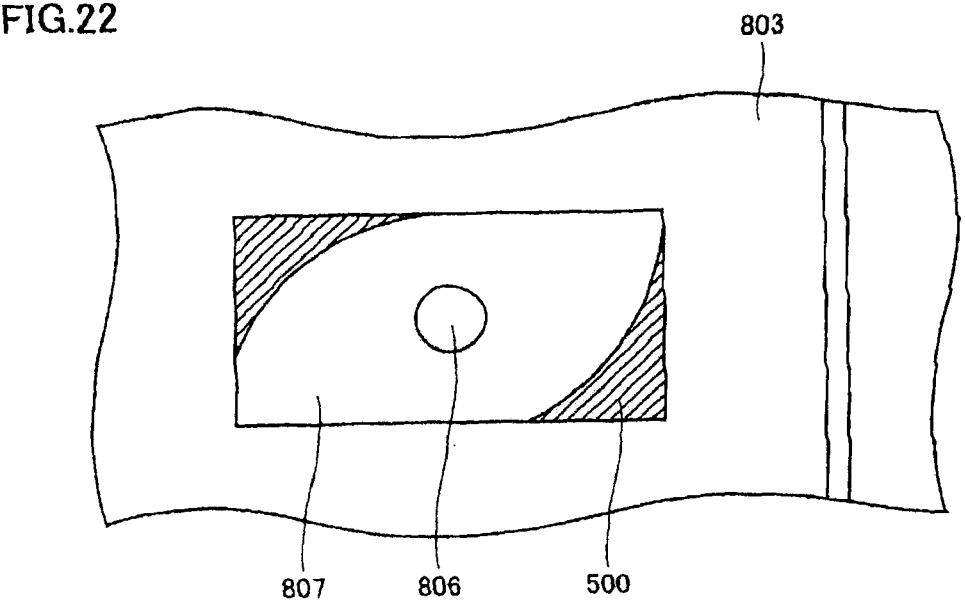
FIG. 22 is a cross-section taken along the line XXII-XXII of FIG. 21.

FIG. 21 is a cross-section showing another form of the microchip in accordance with an embodiment. FIG. 22 is a cross-section taken along the line XXII-XXII of FIG. 21. In the following, description will be given with reference to FIGS. 21 and 22.

In the present embodiment, "upper in the thickness direction" refers to the direction to the third substrate 801 in the thickness direction, and "lower in the thickness direction" refers to the direction to the second substrate 802 in the thickness direction.

The embodiment is similar to the second embodiment in that it includes the second substrate 802, the first substrate 809, the third substrate 801, the first fluid circuit 807, the second fluid circuit 808, through hole 805 and projections 803 and 804.

It is noted, however, that projection 803 extends over the surface of second fluid circuit 808 on the side of the first substrate 809, and that the inner wall of projection 803 forms through hole 805. When centrifugal force is applied in the direction to the left of FIG. 21, the fluid moves from the second fluid circuit 808 to the first fluid circuit 807, and after moved to the second fluid circuit 808, fluid 500 does not move from the first fluid circuit no matter in which direction of FIG. 22 the centrifugal force is applied.

In order to realize such an operation, the through hole 805 is designed such that its cross-section in the direction parallel to the microchip is made smaller than the cross-section of first fluid circuit 807 in the direction parallel to the microchip. Further, in the present embodiment, projections 803 and 804 extend in the direction parallel to the microchip, substantially forming the first fluid circuit 807. Further, in order to enable smooth movement of fluid 500 from the second fluid circuit 808 to the first fluid circuit 807, air vent 806 is formed.

From the foregoing, the area of microchip when the microchip is viewed from above can be made smaller than in the prior art. Thus, the microchip can be reduced in size.

Eighth Embodiment

Figure 23:
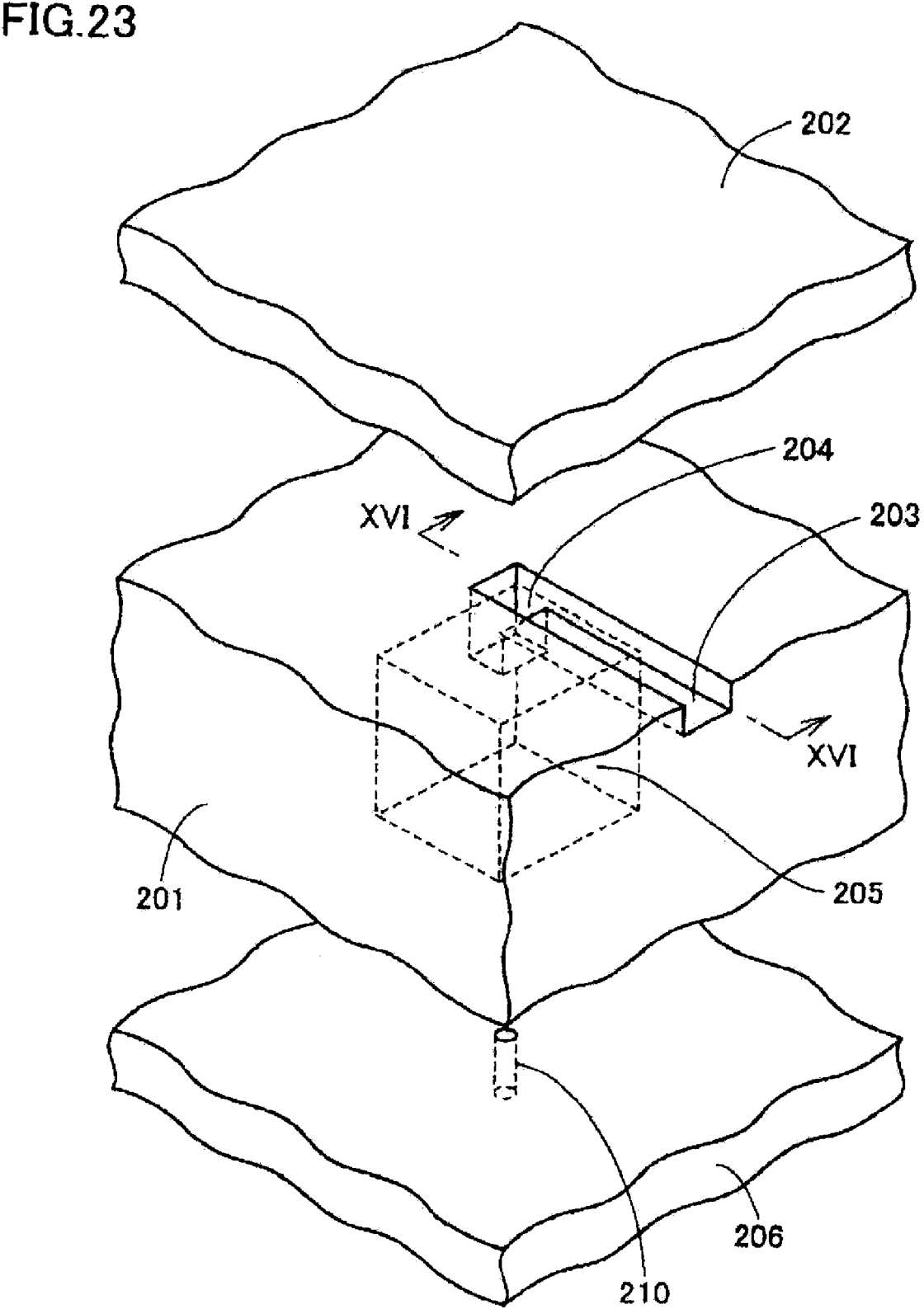
FIG. 23 is a schematic perspective view showing the excess storage in the microchip in accordance with an eighth embodiment of the present invention.
Figure 24:
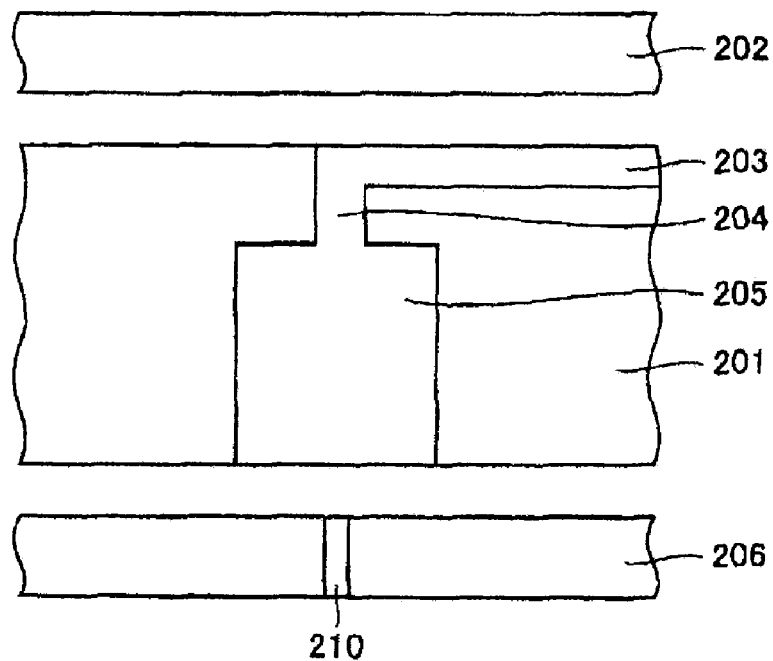
FIG. 24 is a cross-section of the first substrate of FIG. 23, taken along the line XVI-XVI.

FIG. 23 is a schematic perspective view showing an example of a conventional excess storage in a microchip in accordance with an embodiment of the present invention. FIG. 24 is a cross-section taken along the line XVI-XVI of the first substrate shown in FIG. 23.

In the following, description will be given with reference to FIGS. 23 and 24. Further, in the present example and the second example, "upper surface" refers to the surface of first substrate 201 that is joined to the second substrate 202, and "lower surface" refers to the surface of first substrate 201 that is joined to the third substrate 206. Further, "upper in the thickness direction" refers to the direction to the upper surface in the thickness direction and "lower in the thickness direction" refers to the direction to the lower surface in the thickness direction. The second substrate 202 and the third substrate 206 may be transparent substrates, and the first substrate 1 may be a non-transparent substrate or a black substrate.

The microchip in accordance with the present embodiment is formed by joining the third substrate 206, the first substrate 201 having trenches formed on opposite surfaces of the substrate, and the second substrate 2 in order, and has a fluid circuit formed by the trench and the surface of the second substrate 202 facing the first substrate 201, and a fluid circuit formed by the trench and the surface of third substrate 206 facing the first substrate 201. The fluid circuit includes an excess storage 205 formed inside the first substrate 201, a first flow path 203 formed on the upper surface of first substrate to introduce fluid to the excess storage 205, and a coupling flow path 4 coupling the excess storage 205 to the first flow path 203. Here, opposite ends of coupling flow path 204 are coupled to an end of the first flow path 203 and to a surface forming the excess storage 205, that is, the surface forming the upper side in the thickness direction of the present embodiment, respectively, and the end portion of the first flow path 203 and the surface forming the excess storage 205 are at different positions in the thickness direction of the microchip. Further, the surface forming the lower side in the thickness direction of excess storage 205 is the surface of third substrate 206. Further, in the present embodiment, air vent 210 is provided in the third substrate 206. Air vent 210 may be provided at any appropriate position.

The first flow path 203 is continuous to a part of flow path in the microchip. The first flow path 203 is for introducing excess fluid, to excess storage 205 for containing excess fluid unnecessary for examination, such as specimen determined to be excessive at measuring of specimen and liquid reagent, or specimen containing liquid reagent or component that is not an object after centrifugal separation. In the present embodiment, the excess storage has a rectangular parallelepiped shape, and the upper surface in the thickness direction of microchip that is connected to coupling flow path 204 is formed lower in the thickness direction than the lowermost surface in the thickness direction of the end portion of first flow path 203 coupled to the coupling flow path. Further, though the excess storage 205 has a rectangular parallelepiped shape in the present embodiment, it is not limiting, and it may have a spherical shape or substantially spherical shape. Further, excess storage 205 and coupling flow path 204 are preferably formed to have such depth that does not hinder design of flow path in the microchip.

Further, if excess storage 205 has a rectangular parallelepiped shape, lengths in the longer and shorter sides may be set, for example, in the range of 2 to 10 mm. Further, the length of excess storage in the thickness direction may be set, for example, in the range of 1 to 10 mm.

In the present embodiment, coupling flow path 4 is formed parallel to the thickness direction of the microchip. The coupling flow path 204, however, may be formed oblique to the thickness direction of microchip, and what is necessary is that an end portion of coupling flow path 204 is at a different height in the thickness direction of the microchip.

Coupling flow path 204 is preferably formed substantially at the center of the upper surface of the wall forming excess storage 205, as it allows application of centrifugal force in every direction. The position of coupling flow path 204 is not limited, however, dependent on the direction of applying centrifugal force.

Next, an exemplary operation of the microchip in accordance with the present embodiment will be described. The method of operation below is only an example and not limiting. First, a specimen or liquid reagent as the fluid is measured or mixed in the fluid circuit of microchip, and fluid that is eventually unnecessary is fed to the first flow path 203 of first substrate 1. Next, centrifugal force is applied in the direction to the left of FIG. 24 (hereinafter simply referred to as the direction to the left. The same applies to other directions in the following), and the fluid is contained in excess storage 205.

After contained in excess storage 205, the fluid never flows back to the first flow path 203 no matter in which of left, right, forward and backward directions of FIG. 24 the centrifugal force is applied. Therefore, there is no restriction on the order of applying centrifugal force.

From the foregoing, the area of microchip when viewed from above can be reduced to about ⅓ of the conventional example. This contributes to reduction in size of the microchip. Further, it becomes unnecessary to limit the order of applying centrifugal force after the fluid is contained in the excess storage. Therefore, there is a higher degree of freedom in designing the order of applying centrifugal force to the microchip.

Materials of substrates forming the microchip in accordance with the present invention are not specifically limited. Available examples include: organic materials such as polyethylene terephthalate (PET), polybutylene terephthalate (PBT), polymethylmethacrylate (PMMA), polycarbonate (PC), polystyrene (PS), polypropylene (PP), polyethylene (PE), polyethylene naphthalate (PEN), poly arylate resin (PAR), acrylonitrile-butadiene-styrene resin (ABS), vinyl chloride resin (PVC), polymethylpentene resin (PMP), polybutadiene resin (PBD), biodegradable polymer (BP), cycloolefin polymer (COP), polydimethylsiloxane (PDEM); and inorganic materials such as silicon, glass and quartz.

The method of forming excess storage 205 in the microchip in accordance with the present embodiment is not specifically limited, and injection molding using a mold having a transfer structure, imprinting or the like may be used. When the substrate is formed by using inorganic material, etching is also possible.

Ninth Embodiment

Figure 25:
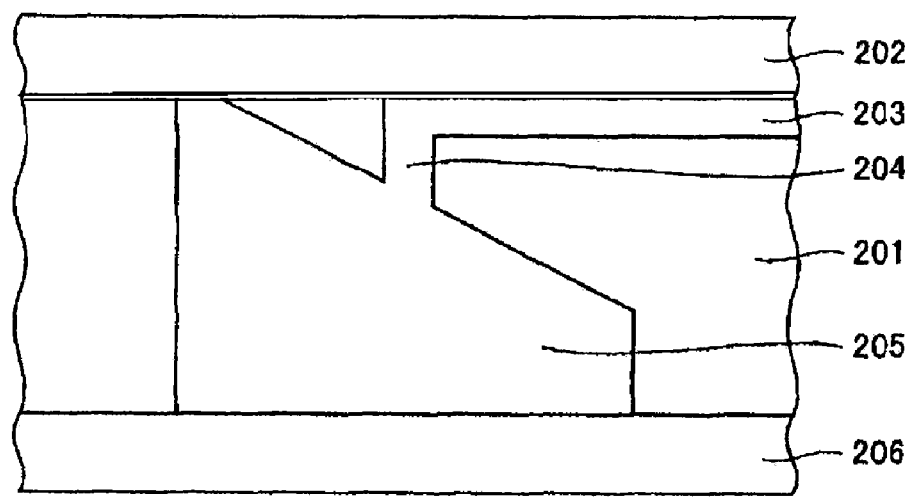
FIG. 25 is a schematic cross-section showing the excess storage in the microchip in accordance with a ninth embodiment of the present invention.
Figure 26:
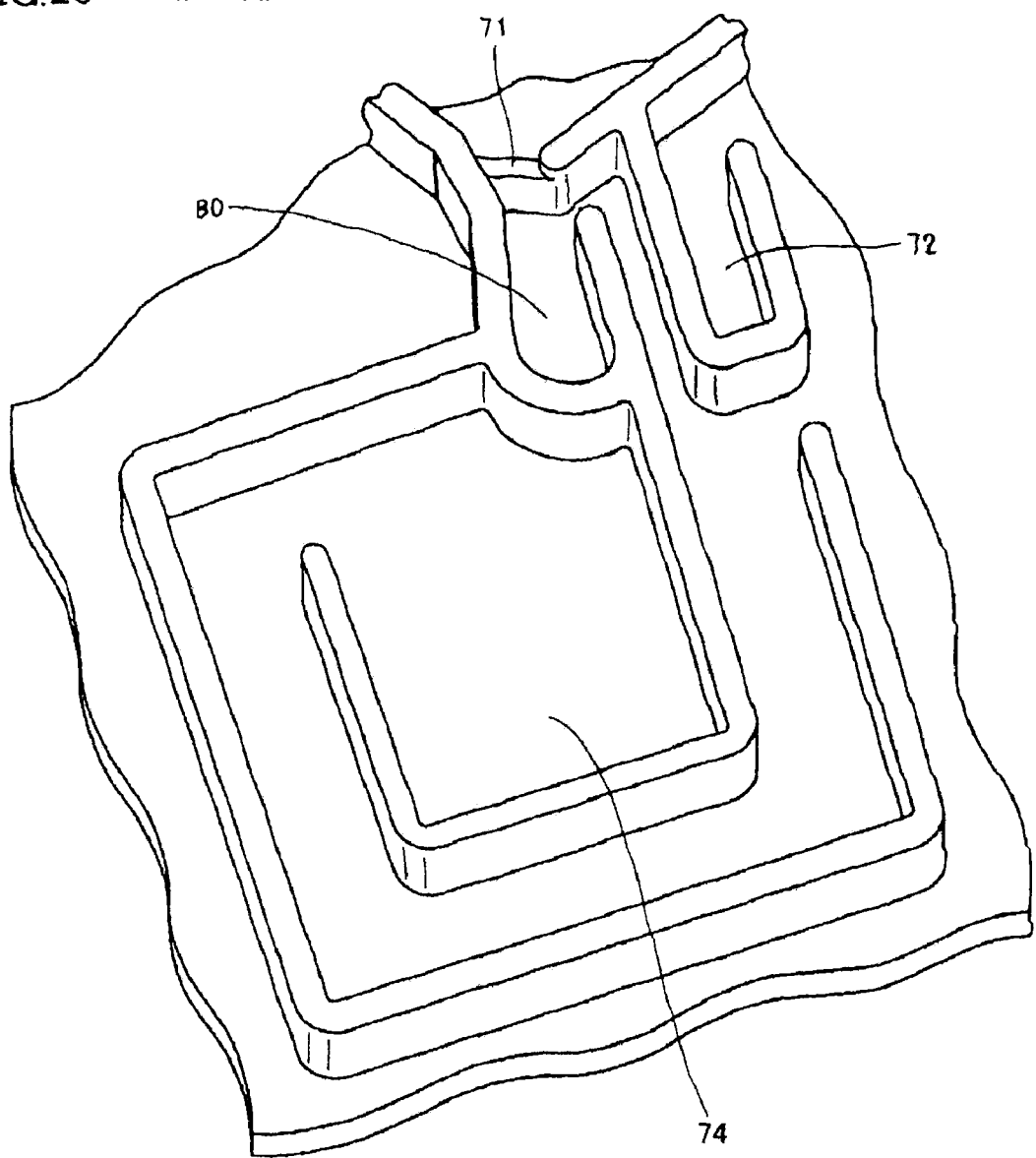
FIG. 26 is a schematic perspective view showing an example of the measuring section and the excess storage in a conventional microchip.
Figure 27:
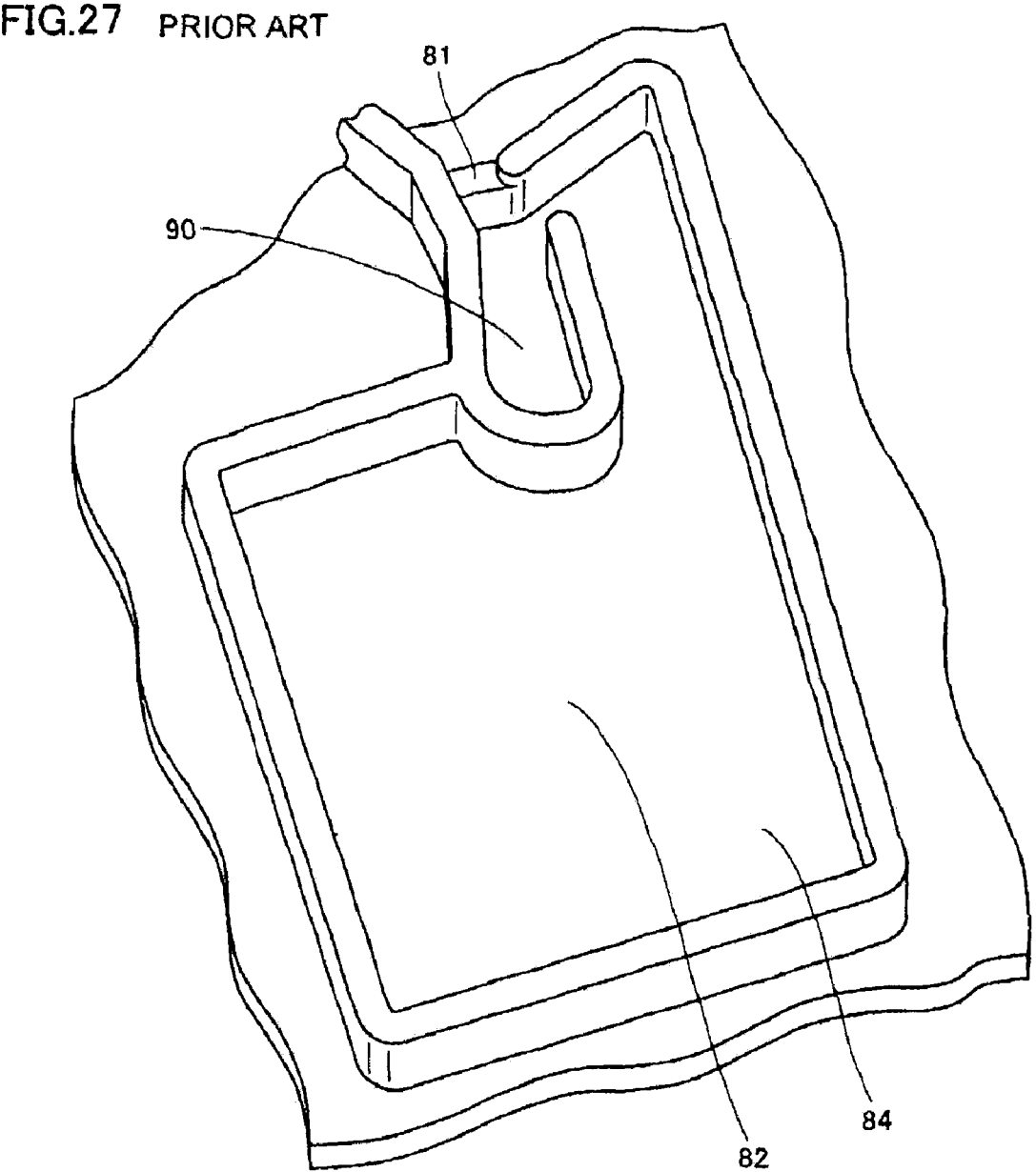
FIG. 27 is a schematic perspective view showing another example of the measuring section and the excess storage in a conventional microchip.
Figure 28:
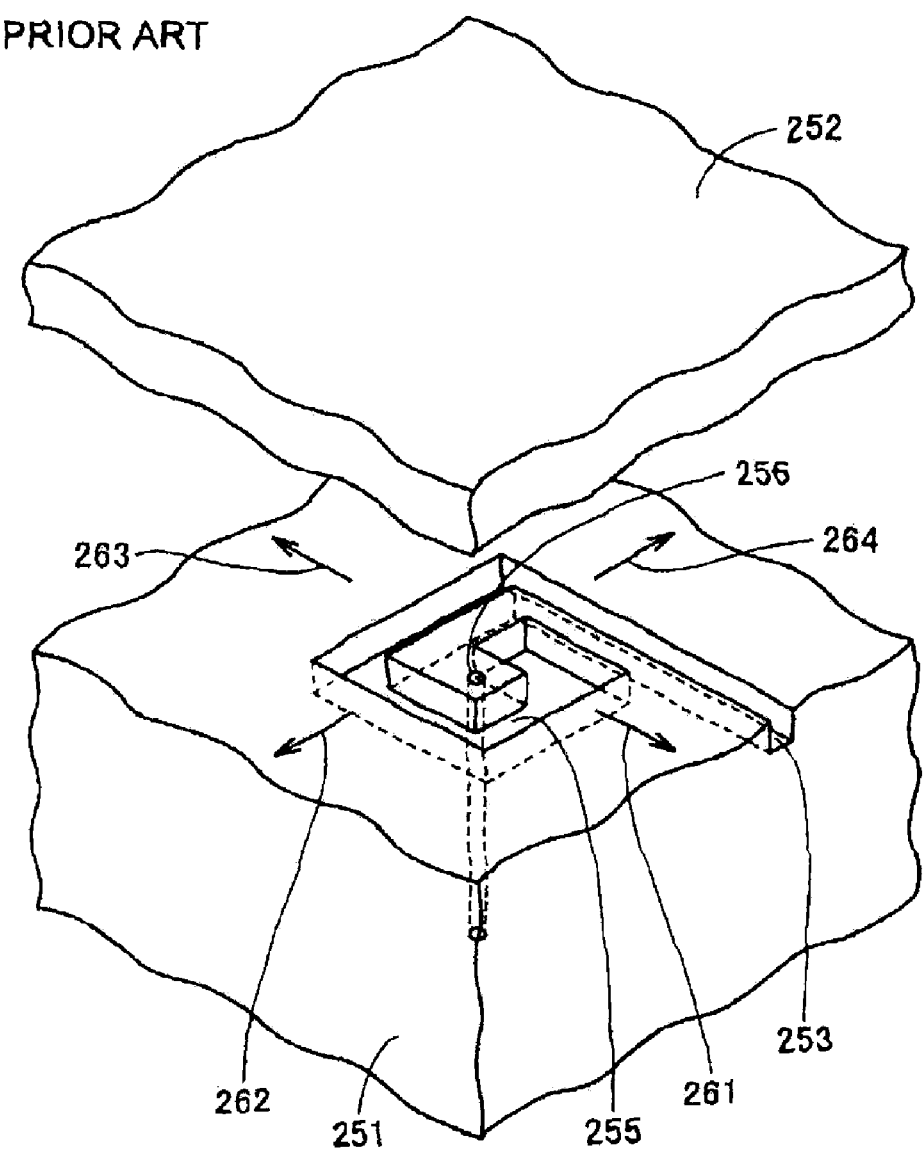
FIG. 28 is a schematic perspective view showing an example of a conventional excess storage of a microchip.
Figure 29:
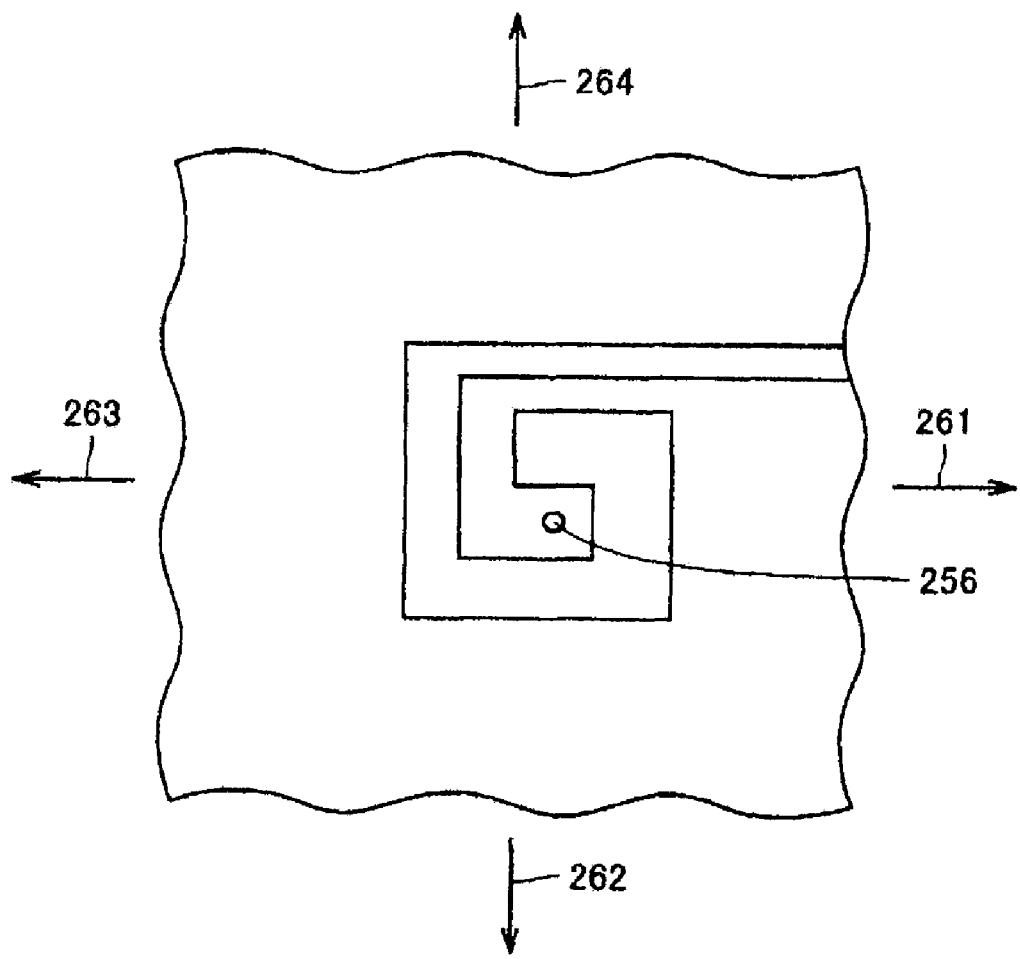
FIG. 29 is a schematic plan view showing an example of a conventional excess storage of a microchip.

FIG. 25 is a schematic cross-section showing an example of excess storage in the microchip in accordance with another embodiment of the present invention.

In the following, description will be given with reference to FIG. 25. In the present embodiment, as described in the first embodiment, the fluid circuit includes excess storage 205 provided inside the first substrate 201, first flow path 203 formed on the upper surface of first substrate to introduce fluid to excess storage 205, and coupling flow path 204 coupling excess storage 205 and first flow path 203. Opposite ends of coupling flow path 204 are coupled to the end portion of first flow path 203 and to the surface forming excess storage 205, that is, the surface forming the upper side in the thickness direction of the present embodiment, respectively. The end portion of the first flow path 203 and the surface forming the excess storage 205 are at different positions in the thickness direction of the microchip. The surface forming the lower side in the thickness direction of excess storage 205 is the surface of third substrate 206.

In the present embodiment, the surface forming the upper side in the thickness direction of excess storage 205 is inclined. Even with such a shape as shown in 25, it is possible to attain effects similar to those attained by the first embodiment, as long as the end portion of first flow path 203 and the surface forming excess storage 205 (in the present embodiment, the surface forming the upper side in the thickness direction of excess storage 205) are at different positions in the thickness direction of the microchip.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip comprising a first substrate joined to a second substrate, the first substrate including a trench in its surface, wherein the trench and a surface of said second substrate facing said first substrate form first and second fluid circuits, the microchip further comprising:
    a through hole or air vent in one of the substrates so as to connect the fluid circuits to outside the microchip, wherein the first fluid circuit is located to a first side of the through hole or air vent and wherein the second fluid circuit is located to a second side of the through hole or air vent,
    a first projection located at a position between the first fluid circuit and the through hole or air vent, and a second projection located at a position between the second fluid circuit and the through hole or air vent,
    wherein a separation distance between the first projection and a surface of one of the substrates is smaller than a separation distance between the second projection and the surface of the one of the substrates.

2. The microchip of claim 1 wherein at least one of the projections has an inclined sidewall near said through hole or air vent.

3. The microchip according to claim 2, wherein the inclined sidewall of said projection is inclined with respect to said first substrate.

4. The microchip of claim 1 wherein the through hole or air vent connecting said fluid circuit to the outside of said microchip is in the first substrate; and
    the projections arc on a surface of said first substrate.

5. The microchip according to claim 4, wherein surfaces forming each of the projections are inclined with respect to said second substrate.

6. A microchip comprising a first substrate joined to a second substrate, and a third substrate joined to the first substrate, wherein said first substrate has trenches formed on opposite surfaces;
    the microchip further comprising:
    a first fluid circuit formed by a first one of the trenches and a surface of said second substrate facing said first substrate, and
    a plurality of second fluid circuits formed by a second one of the trenches and a surface of said third substrate facing said first substrate;
    wherein said first substrate has a through hole connecting said first fluid circuit and said second fluid circuits;
    first and second projections on the first substrate extending respectively toward the third substrate,
    wherein the first projection is located at a position between a first one of the second fluid circuits and the through hole, and the second projection is located at a position between a second one of the second fluid circuits and the through hole, and
    wherein a separation distance between the first projection and a surface of the third substrate is smaller than a separation distance between the second projection and the surface of the third substrate.

7. The microchip according to claim 6, further comprising a first wall surface connecting the surface of said second substrate forming said first fluid circuit and an inner wall forming said through hole, and shutting off said first fluid circuit; wherein
    said first wall surface and the inner wall forming said through hole are inclined to said third substrate.

8. The microchip according to claim 6, wherein a respective surface of each of the projections facing the through hole is inclined with respect to said third substrate.

9. The microchip of claim 6 wherein a cross-section of the through hole in a direction parallel to a top surface of said microchip is smaller than a cross-section of the first fluid circuit in a direction parallel to the top surface of said microchip.

* * * * *